United States Patent [19]

Bacque et al.

[11] Patent Number: 5,556,861

[45] Date of Patent: Sep. 17, 1996

[54] 1,8 BENZONAPHTHYRIDINE DERIVATIVES AND ANTIMICROBIAL COMPOSITIONS

[75] Inventors: Eric Bacque, Morsang-sur-Orge; Michel Barreau, Montgeron; Jean-Francois Desconclois, Paris; Philippe Girard, Arpajon; Michel Kryvenko, Paris; Marc P. Lavergne, Mandres-les-Roses; Jean-Marc Paris, Vaires-sur-Marne; Guy Picaut, Villejuif, all of France

[73] Assignee: Laboratoire Roger Bellon, Neuilly-sur-Seine, France

[21] Appl. No.: 472,766

[22] Filed: Jun. 7, 1995

Related U.S. Application Data

[63] Continuation of Ser. No. 211,317, Apr. 1, 1994, abandoned.

[30] Foreign Application Priority Data

Oct. 1, 1991 [FR] France ................... 91 12058

[51] Int. Cl.[6] .................. A61K 31/435; C07D 471/04
[52] U.S. Cl. .................. 514/292; 546/81
[58] Field of Search .................. 546/81, 83, 156; 514/292

[56] References Cited

U.S. PATENT DOCUMENTS

| | | | |
|---|---|---|---|
| 4,670,444 | 6/1987 | Grohe | 514/300 |
| 4,767,762 | 8/1988 | Chu | 514/254 |
| 4,927,926 | 5/1990 | Corgminas | 544/101 |
| 5,004,745 | 4/1991 | Antoine | 514/254 |
| 5,087,621 | 2/1992 | Pinol | 514/210 |

Primary Examiner—C. Warren Ivy
Assistant Examiner—Evelyn Huang
Attorney, Agent, or Firm—Finnegan, Henderson, Farabow, Garrett & Dunner, L.L.P.

[57] ABSTRACT

This invention relates to a novel 1,8 benzo[b]naphythyridine derivative of general formula (I),

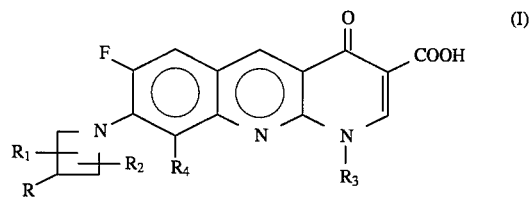

wherein R is H or a hydroxy, amino or alkylamino radical optionally substituted by amino or hydroxy, or R is dialkylamino of which the alkyl portions may form, with the nitrogen atom, a 5- or 6-membered heterocyclic ring which optionally contains a further heteroatom chosen from nitrogen, oxygen or sulphur, or R is $C_{3-6}$ cycloalkylamino or an alkanylamino, N-alkyl N-alkanylamino or aminoalkylphenylamino radical; $R_1$ and $R_2$, which are the same or different, are in positions 2 and 3 and represent H, alkyl, $C_{2-4}$ alkenyl, phenyl, or substituted phenyl, or $R_1$ and $R_2$ are in position 2 and represent alkyl; $R_3$ is H or alkyl, fluoroalkyl, carboxyalkyl, $C_{3-6}$ cycloalkyl, fluorophenyl, difluorophenyl, alkyloxy or alkylamino; and $R_4$ is H or F, wherein the $C_{1-4}$ alkanyl and alkyl radicals are linear or branched; stereoisomeric forms thereof or mixtures of these; and salts and hydrated forms thereof. These novel derivatives are useful as antimicrobials.

14 Claims, No Drawings

1,8 BENZONAPHTHYRIDINE DERIVATIVES AND ANTIMICROBIAL COMPOSITIONS

This is a continuation of application Ser. No. 08/211,317, filed on Apr. 1, 1994 abandoned, which is the national phase of PCT/FR 92/00901, filed Sep. 29, 1992, published as WO93/07144, Apr. 15, 1993.

FIELD OF THE INVENTION

The present invention relates to new benzo[b][1,8]naphthyridine derivatives of general formula:

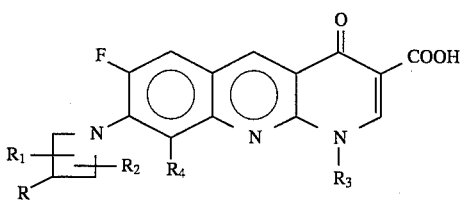

to their salts, to their preparation and to compositions containing them.

BACKGROUND OF THE INVENTION

In Patent Application EP 431,991, benzonaphthyridine derivatives of structure:

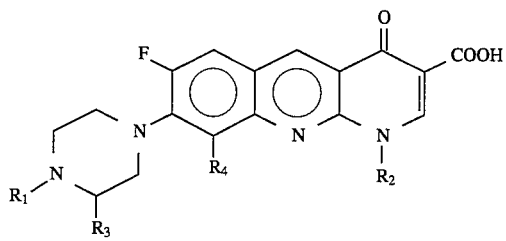

in which $R_1$ is H, hydroxy or alkyl, $R_2$ is H, alkyl, fluoroalkyl, cycloclalkyl, alkyloxy or alkylamino, $R_3$ is phenyl or phenylalkyl, optionally substituted, and $R_4$ is H or a fluorine atom, have been described. These products are useful as antimicrobial agents.

DESCRIPTION OF THE INVENTION

It has been found that the products of general formula (I) in which:

- R represents a hydrogen atom or a hydroxyl or amino radical or an alkylamino radical in which the alkyl portion is optionally substituted with an amino or hydroxyl radical, or represents a dialkylamino radical in which the alkyl portions, with the nitrogen atom to which they are attached, can optionally form a 5- or 6-membered haterecycle optionally containing another hetero atom chosen from nitrogen, oxygen and sulphur, or represents a (3- to 6-membered cycloalkyl)amino radical, or an alkanoylamino, N-alkyl-N-elkenoylamino or aminoalkylphenylamino radical,
- $R_1$ and $R_2$, which my be identical or different, are located, respectively, at positions 2 and 3 and represent hydrogen atoms, alkyl radicals, alkenyl radicals containing 2 to 4 carbon atoms, phenyl radicals or phenyl radicals substituted with a halogen atom or with an alkyl, alkyloxy, hydroxyl, nitro, amino, alkylamino, dialkylamino or haloalkyl radical, or alternatively $R_1$ and $R_2$ are located at position 2 and represent alkyl radicals,
- $R_3$ represents a hydrogen atom or an alkyl, fluoroalkyl or carboxyalkyl radical, a cycloalkyl radical containing 3 to 6 carbon atoms or a fluorophenyl, difluorophenyl, alkyloxy or alkylamino radical, and
- $R_4$ represents a hydrogen atom or a fluorine atom, the alkyl and alkanoyl radicals mentioned above being unbranched or branched and containing 1 to 4 carbon atoms, as well as their salts and, where appropriate, their stereoisomers, manifest especially advantageous antibacterial activity.

When R represents a dialkylamino radical in which the alkyl portions, with the nitrogen atom, form a heterocycle, the latter can be, in particular, pyrrolidinyl or piperidyl.

The products of general formula (I) can exist in the state of a hydrated form; it is understood that these hydrates also fall within the scope of the present invention.

According to the invention, the products of general formula (I) may be obtained by substitution of an azetidine of general formula:

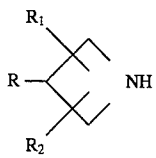

in which R, $R_1$ and $R_2$ are defined as above, with a benzo[b][1,8]naphthyridine of general formula:

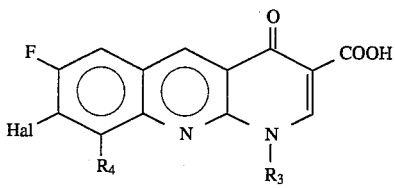

in which $R_3$ is defined as above, Hal is a fluorine, chlorine or bromine atom if $R_4$ is hydrogen, or alternatively Hal and $R_4$ are simultaneously fluorine atoms.

The action of the azetidine derivative of general formula (II) is generally performed in the presence of an excess of this derivative as acid-acceptor in suitable organic solvents. It is possible to work with or without a solvent, at a temperature of between 20° and 150° C. When the working conditions include the presence of a solvent, the reaction is advantageously performed in solvents such as pyridine, dimethylformamide, dimethyl sulphoxide or acetonitrile. It is also possible to work in an aqueous medium.

It can also be advantageous to work in the presence of an acid-acceptor such as, e.g., a nitrogenous organic base (triethylamine in particular), an alkali metal carbonate (e.g. sodium carbonate) or an alkali metal or alkaline earth metal hydroxide.

It is understood that, in the case where the symbol $R_3$ of the product of general formula (III) is a hydrogen atom, or when R is an amino, optionally substituted alkylamino, cycloalkylamino or aminoalkylphenylamino radical, it is preferable to protect the starting material beforehand. The protection and removal of the protective radical after the reaction are performed according to the customary methods.

The protection may be carried out with any compatible group whose use and removal has no adverse effect on the remainder of the molecule. In particular, the methods employed are those described by T. W. GREENE, Protective Groups in Organic Synthesis, A. Wiley-Interscience Publication (1981), or by McOMIE, Protective Groups in Organic Chemistry, Plenum Press (1973).

As an example, the protective groups may be chosen from trimethylsilyl, benzhydryl, tetrahydropyranyl, formyl, acetyl, chloroacetyl, trichloroacetyl, trifluoroacetyl, ethoxycarbonyl, t-butoxycarbonyl and trichloroethoxycarbonyl radicals.

According to the invention, the benzo[b][1,8]naphthyridine derivatives of general formula (I) may also be obtained from the corresponding ester of general formula:

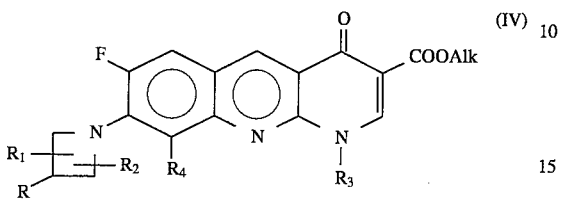
(IV)

in which $R_1$, $R_2$ and $R_4$ are defined as above, R is defined as above or represents a protected amino radical, $R_3$ is defined as above or represents a protected alkylamino radical and Alk represents an unbranched- or branched-chain alkyl radical containing 1 to 4 carbon atoms, by any known method for obtaining an acid from an ester without affecting the remainder of the molecule.

The preparation of the acid from the ester is generally performed by saponification in the presence of potassium hydroxide or sodium hydroxide, in an aqueous or aqueous-alcoholic medium, at a temperature of between 20° and 100° C.

In the case where an ester of general formula (IV) for which R is an alkanoylamino or N-alkyl-N-alkanoylamino radical or for which R is a protected amino radical is hydrolysed, it is understood that, depending on the conditions employed, the product obtained is either the acid for which R is an alkanonylamino or N-alkyl-N-alkanoylamino radical or for which R is a protected amino radical, or the acid for which hydrolysis of the amide has been performed simultaneously, i.e. for which R is an amino radical. The working conditions are chosen in accordance with the expected final product. When R is a protected amino radical, it is naturally advantageous to remove the protective radical simultaneously.

When $R_3$ represents a protected alkylamino radical, the protective radical can be any amino-protective group compatible with the molecule. It is especially advantageous to choose a protective radical which can be removed simultaneously with the hydrolysis of the ester.

The benzo[b][1,8]naphthyridine derivative of general formula (III) may be obtained from the corresponding ester of general formula:

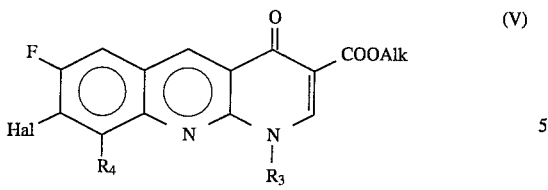
(V)

in which $R_3$, $R_4$, Hal and Alk are defined as above, by application of the method described in U.S. Pat. No. 4,990,515 or by a technique analogous to that described.

The ester derived from benzo[b][1,8]naphthyridine of general formula (V) may be prepared by the action of 3-amino-1,2,4-triazine (to obtain a product for which $R_3$ is a hydrogen atom), or by the action of a product of general formula:

$R_3$—$NH_2$ (VI)

in which $R_3$ is alkyl, fluoroalkyl, carboxyalkyl, cycloalkyl, fluorophenyl, difluorophenyl, alkyloxy or alkylamino, optionally protected, on a quinoline derivative of general formula:

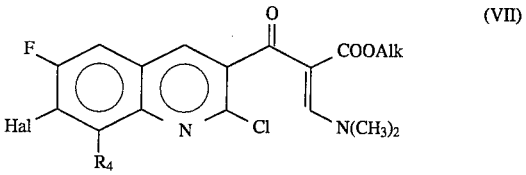
(VII)

in which $R_4$, Hal and Alk are defined as above, followed by cyclization by the action of an acid-acceptor agent.

In general, the reaction of 3-amino-1,2,4-triazine or of the product of general formula (VI) is carried out in an organic solvent such as an alcohol (e.g. ethanol, methanol) or a chlorinated solvent (e.g. trichloromethane), at a temperature of between 10° and 25° C.

The cyclization is performed in an unbranched- or branched-chain alcohol containing 1 to 4 carbon atoms, at a temperature between 20° C. and the refluxing temperature of the reaction mixture.

The acid-acceptor agent can be, in particular, chosen from nitrogenous bases (e.g. triethylamine), 1,8-diazabicyclo [5.4.0]undec-7-ene and an excess of the amine employed.

The benzo[b]naphthyridine derivatives of general formula (III) and (V) for which $R_3$ is a carboxyalkyl, fluorophenyl or difluorophenyl radical are new products. It is understood that these products as well as their salts, where they exist, also fall within the scope of the present invention.

The quinoline derivative of general formula (VII) may be obtained as described in U.S. Pat. No. 4,990,515.

The aminoazetidine derivatives of general formula (II) may be prepared according to the processes described by: T. Okutani et al. Chem. Pharm. Bull., 22 (7) 1490 (1974); S. Chatterjee et al. Chem. Comm., 93 (1968); D. Nisato et al. J. Heterocyclic. Chem., 22, 961 (1985); Akira Morimoto et al., Chem. Pharm. Bull., 21 (1), 228 (1973); A. G. Anderson et al., J. Org. Chem., 37, 3953 (1972); V. R. Gaertner., J. Org. Chem., 2972 (1967), J. N. Wells et al., J. Org. Chem., 34, 1477 (1969), J. Antibiotics, 39 (9), 1243 (1986) and J. Pharm. Soc., 60 (1), 156 (1971); EP 406,112; EP 314,362; EP 106,489; EP 324,298; JP 74/109,369 [C.A.83–9760 (1975)]; U.S. Pat. No. 4,834,846 or by methods analogous to these.

3-Amino-3-phenylazetidine may be obtained by reduction of the corresponding 2-azetidinone, according to the method described in J. Pharm. Sci., 60, 5, (1971). 3-Amino-3-phenyl-2-azetidinone is prepared by a method analogous to that described in J. Am. Chem. Soc., 111, 1073 (1989) followed by liberation of the radical protecting the amine.

The benzo[b][1,8]naphthyridine derivative of general formula (IV) may be obtained from the benzo[b]-naphthyridine of general formula (V) by substitution of an azetidine derivative of general formula (II).

It is advantageous to work under the conditions described above for obtaining a product of general formula (I) from an azetidine of general formula (II) and a benzo[b][1,8]naphthyridine of general formula (III). It is understood that, in the option or the reaction is performed in an aqueous medium, the product of general formula (I) may be obtained directly without isolating the intermediate derivative of general formula (IV).

According to the invention, where appropriate, when it is desired to obtain the stereo-isomers of the benzonaphthyridine derivatives of general formula (I), the separation of the stereo-isomeric forms of the azetidines of general formula (II) is performed by any known method which is compatible with the molecule. As an example, the separation is performed by acylation by means of a chiral acid or reactive derivative of a chiral acid, separation of the isomers by high performance liquid chromatography and then deacylation according to the method described by P. G. Gaseman et al., J. Am. Chem. Soc., 9.8 (5), 1275 (1976). It is also possible to perform the separation of the stereoisomers by chiral-phase high performance liquid chromatography.

The new products according to the present invention, as well as their synthesis intermediates, can be optionally purified by physical methods such as crystallisation or chromatography.

The products according to the present invention, as well as their intermediates of general formula (III) and, where appropriate, their intermediates of general formula (V), may be converted to metal salts or to addition salts with nitrogenous bases according to methods known per se. These salts may be obtained by the action of a metal-containing base (containing, e.g., an alkali metal or alkaline earth metal), ammonia or an amine on a product according to the invention in a suitable solvent such as an alcohol, an ether or water, or by an exchange reaction with a salt of an organic acid. The salt formed precipitates after concentration, where appropriate, of its solution; it is separated by filtration, decantation or lyophilization.

The new products according to the invention may also be converted to addition salts with acids. The products of general formula (I) obtained in the form of these salts may be liberated and converted to salts of other acids according to the customary methods.

As examples of pharmaceutically acceptable salts, there may be mentioned the salts with alkali metals (sodium, potassium, lithium) or with alkaline earth metals (magnesium, calcium), the ammonium salt, the salts of nitrogenous bases (ethanolamine, diethanolamine, trimethylamine, triethylamine, methylamine, propylamine, diisopropylamine, N,N-dimethylethanolamine, benzylamine, dicyclohexylamine, N-benzylphenethylamine, N,N'-dibenzylethylenediamine, diphenylenediamine, benzhydrylamine, quinine, choline, arginine, lysine, leucine, dibenzylamine), as well as the addition salts with inorganic acids (hydrochlorides, hydrobromides, sulphates, nitrates, phosphates) or organic acids (succinates, fumarates, maleates, methanesulphonates, p-toluenesulphonates, isethionates).

The new benzo[b][1,8]naphthyridine derivatives of general formula (I) according to the present invention and their pharmaceutically acceptable salts exhibit especially advantageous antibacterial properties. They manifest exceptional activity in vitro and in vivo against Gram-positive microorganisms and, generally, against the microorganisms responsible for most infections of the upper and lower airways. Furthermore, the new benzo[b][1,8]naphthyridine derivatives of general formula (I) manifest especially advantageous antibacterial activity against Gram-negative microorganisms.

In vitro, the products of general formula (I) were shown to be active at a concentration of between 0.06 and 4 µg/cc against Staphylococcus aureus IP 8203, and at a concentration of between 0.25 and 20 µg/cc against Escherichia coli strain NIRJ JC2.

In vivo, the products of general formula (I) were shown to be active against experimental Staphylococcus aureus IP 8203 infections of mice at oral doses of between 2 and 200 mg/kg.

Moreover, some of the products according to the invention proved especially advantageous against mycoplasma.

Their minimal inhibitory concentration is between 0.03 and 8 µg/ml.

Lastly, the products according to the invention exhibit no toxicity at the doses used. They are generally non-toxic at oral doses of 500 mg/kg in mice.

EXAMPLES

The examples which follow, given without implied limitation, illustrate the present invention.

Example 1

8-(3-Amino-1-azetidinyl)-7-fluoro-1-methyl-4-oxo-1,4-dihydrobenzo[b][1,8]naphthyridine-3-carboxylic acid A suspension of 1.16 g of 7,8-difluoro-1-methyl-4-oxo-1,4-dihydrobenzo[b][1,8]naphthyridine-3-carboxylic acid and 1.38 g of 3-aminoazetidine in 15 cm$^3$ of dimethyl sulphoxide is heated with stirring to a temperature in the region of 95° C. for 6 hours. After cooling to approximately 20° C., 100 cm$^3$ of water are added to the reaction mixture. The insoluble matter is drained, washed with 3 times 20 cm$^3$ of water, taken up with 100 cm$^3$ of water and treated with 4 cm$^3$ of N methanesulphonic acid. After removal of some slight insoluble matter by filtration through diatomaceous silica and addition of 4 cm$^3$ of N aqueous sodium hydroxide, the suspension obtained is concentrated under reduced pressure (20 kPa) at a temperature in the region of 60°C. to a volume of approximately 80 cm$^3$. The insoluble matter is drained, washed with 100 cm$^3$ of water and 100 cm$^3$ of ethanol and recrystallized in 150 cm$^3$ of dimethylformamide. 0.7 g of 8-(3-amino-1-azetidinyl)-7-fluoro-1-methyl-4-oxo1,4-dihydrobenzo[b][1,8]naphthyridine-3-carboxylic acid is obtained in the form of a yellow solid, which decomposes at 358° C.

7,8-Difluoro-1-methyl-4-oxo-1,4-dihydrobenzo[b][1,8]naphthyridine-3-carboxylic acid is prepared as described in U.S. Pat. No. 4,990,515.

3-Aminoazetidine was prepared according to the method described by Dino Nisato et al., J. Het. Chem., 22, 961, (1985).

Example 2

8-(3-Dimethylamino-1-azetidinyl)-7-fluoro-1-methyl-4-oxo-1,4-dihydrobenzo[b][1,8]naphthyridine-3-carboxylic acid A suspension of 1.9 g of 8-(3-dimethylamino-1-azetidinyl)-3-ethoxycarbonyl-7-fluoro-1-methyl-4-oxo1,4-dihydrobenzo[b][1,8]naphthyridine in 20 cm$^3$ of ethanol and 19 cm$^3$ of 0.5N aqueous potassium hydroxide is heated with stirring to a temperature in the region of 80° C. for 5 hours. After cooling to approximately 5° C., the reaction mixture is treated with 9.5 cm$^3$ of N aqueous methane sulphonic acid solution. The insoluble matter is drained, washed with twice 10 cm$^3$ of water and 3 times 25 cm$^3$ of ethanol and recrystallized in 125 cm$^3$ of dimethylformamide. 1.4 g of 8-(3 -dimethylamino-1-azetidinyl)-7-fluoro-1-methyl-4-oxo-1,4-dihydrobenzo[b][1,8]naphthyridine-3-carboxylic acid are obtained in the form of a yellow solid, which decomposes at 312° C.

8-(3-Dimethylamino-1-azetidinyl)-3-ethoxy-carbonyl-7-fluoro-1-methyl-4-oxo-1,4-dihydrobenzo[b][1,8]naphthyridine was prepared in the following manner:

A suspension of 2 g of 3-ethoxycarbonyl-7,8-difluoro-1-methyl-4-oxo-1,4-dihydrobenzo[b][1,8]-naphthyridine, 1.2 g of 3-(dimethylamino)azetidine dihydrochloride and 1.5 g of sodium carbonate in 30 cm³ of dimethyl sulphoxide is heated with stirring to a temperature in the region of 95° C. for 5 hours. After cooling to approximately 20° C., the reaction mixture is treated with 60 cm³ of water. The insoluble matter is drained and washed with 3 times 20 cm³ of water. 2 g of 8-(3-dimethylamino-1-azetidinyl)-3-ethoxycarbonyl-7-fluoro-1-methyl-4-oxo-1,4-dihydrobenzo[b][1,8]-naphthyridine are obtained in the form of a yellow solid, melting point 224° C., which is used without further purification for the subsequent steps.

3-Ethoxycarbonyl-7,8-difluoro-1-methyl-4-oxo1,4-dihydrobenzo[b][1,8]naphthyridine may be prepared as described in U.S. Pat. No. 4,970,213.

Example 3

8-(3-Amino-1-azetidinyl)-1-ethyl-7-fluoro-4-oxo-1,4 dihydrobenzo[b][1,8]naphthyridine-3-carboxylic acid The reaction is performed under the conditions described in Example 2, but starting with 0.72 g of 8-(3-amino-1-azetidinyl)-3-ethoxycarbonyl-1 -ethyl-7-fluoro-4-oxo-1,4-dihydrobenzo[b][1,8]-naphthyridine. Without recrystallization, 0.6 g of 8-(3-amino-1-azetidinyl)-1-ethyl-7-fluoro-4-oxo-1,4-dihydrobenzo[b][1,8]naphthyridine-3-carboxylic acid monohydrate is obtained in the form of a yellow solid, which decomposes at 306° C.

8-(3-Amino-1-azetidinyl)-3-ethoxycarbonyl-1 -ethyl-7-fluoro-4-oxo-1,4-dihydrobenzo[b][1,8]-naphthyridine was prepared under the conditions described in Example 2, but starting with 1.7 g of 3-ethoxy-carbonyl-1-ethyl-7,8-difluoro-4-oxo-1,4 dihydrobenzo-[b][1,8]naphthyridine and 1.62 g of 3-aminoazetidine dimethanesulphonate. The crude product is taken up with 100 cm³ of dimethylformamide and stirred for 10 minutes at approximately 150° C. After cooling to approximately 20° C., some insoluble matter is removed by filtration. The filtrate is concentrated to dryness under reduced pressure (20 kPa) at approximately 60° C. The residue is recrystallized in 50 cm³ of ethanol. 0.72 g of 8-(3-amino-1-azetidinyl)-3- ethoxycarbonyl-1-ethyl-7-fluoro-4-oxo-1,4-dihydrobenzo[b][1,8]naphthyridine is obtained in the form of a yellow solid, melting point 255°–256° C.

3-Ethoxycarbonyl-1-ethyl-7,8-difluoro-4-oxo1,4-dihydrobenzo[b][1,8]naphthyridine was prepared as described in U.S. Pat. No. 4,970,213.

Example 4

8-(3-Dimethylamino-1-azetidinyl)-1-ethyl-7-fluoro-4 -oxo-1,4-dihydrobenzo[b][1,8]naphthyridine-3-carboxylic acid The reaction is performed under the conditions described in Example 2, but starting with 2 g of 8-(3-dimethylamino-1-azetidinyl)-3 -ethoxycarbonyl-1-ethyl-7-fluoro-4-oxo-1,4 -dihydrobenzo[b][1,8]naphthyridine. 1.68 g of 8-(3-dimethylamino-1-azetidinyl)-1-ethyl-7-fluoro-4 -oxo-1,4-dihydrobenzo[b][1,S]naphthyridine-3-carboxylic acid are obtained in the form of a yellow solid, which decomposes at 278° C.

8-(3-Dimethylamino-1-azetidinyl)-3-ethoxy-carbonyl-1-ethyl-7-fluoro-4-oxo-1,4-dihydrobenzo[b][1,8]naphthyridine was prepared under the conditions described in Example 2, but starting with 1.7 g of 3-ethoxy-carbonyl-1-ethyl-7,8-difluoro-4-oxo-1,4-dihydrobenzo[b][1,8]-naphthyridine, and 1.3 g of 3-(dimethyl- amino)azetidine dihydrochloride. After reaction, the reaction mixture, cooled to approximately 20° C., is poured into 50 cm³ of water and extracted with 3 times 100 cm³ of dichloromethane. The combined organic extracts are washed with 3 times 150 cm³ of water and dried over magnesium sulphate. After concentration to dryness under reduced pressure (20 kPa) at approximately 40° C. the residue is taken up with 50 cm³ of ethyl ether, filtered off and washed with twice 50 cm³ of the same solvent. 2 g of 8-(3-dimethylamino-1 -azetidinyl)-3-ethoxycarbonyl-1-ethyl-7-fluoro-4-oxo-1,4-dihydrobenzo[b][1,8]naphthyridine are obtained in the form of a yellow solid, melting point 232° C., which is used without further purification for the subsequent steps.

Example 5

8-(3-Amino-1-azetidinyl)-1-cyclopropyl-7-fluoro-4-oxo-1,4-dihydrobenzo[b][1,8]naphthyridine-3-carboxylic acid The reaction is performed under the conditions described in Example 2, but starting with 1 g of 8-(3-amino-1-azetidinyl)-1-cyclopropyl-3-ethoxycarbonyl-7-fluoro-4-oxo-1,4-dihydrobenzo[b][1,8]naphthyridine. 0.56 g of 8-(3-amino-1-azetidinyl)-1-cyclopropyl-7-fluoro-4-oxo-1,4 -dihydrobenzo[b][1,S]naphthyridine-3-carboxylic acid hemihydrate is obtained in the form of a yellow solid, which decomposes at 298°–303° C.

8-(3-Amino-1-azetidinyl)-1-cyclopropyl-3 -ethoxycarbonyl-7-fluoro-4-oxo-1,4-dihydrobenzo-[b][1,8]naphthyridine was prepared under the conditions of Example 2, but starting with 1.7 g of 1-cyclopropyl-3-ethoxycarbonyl-7,8-difluoro-4-oxo-1,4-dihydrobenzo[b][1,8]naphthyridine and 1.88 g of 3-aminoazetidine dimethanesulphonate. After 1 recrystallization in 50 cm³ of ethanol, 1.05 g of 8-(3-amino-1-azetidinyl)-1-cyclopropyl-3-ethoxycarbonyl-7-fluoro-4-oxo-1,4 -dihydrobenzo[b][1,8]naphthyridine are obtained in the form of a yellow solid, melting point 178°–180° C.

1-Cyclopropyl-3-ethoxycarbonyl-7,8-difluoro-4-oxo-1,4-dihydrobenzo[b][1,8]naphthyridine may be prepared as described in U.S. Pat. No. 4,970,213.

Example 6

1-Cyclopropyl-8-(3-dimethylamino-1-azetidinyl)-7 -fluoro-4-oxo-1,4-dihydrobenzo[b][1,8]naphthyridine-3-carboxylic acid The reaction is performed under the conditions described in Example 4, but starting with 1.27 g of 1-cyclopropyl-8-(3-dimethylamino-1 -azetidinyl)-3-ethoxycarbonyl-7-fluoro-4-oxo-1,4-dihydrobenzo[b][1,8]naphthyridine. 0.8 g of 1-cyclopropyl-8-(3-dimethylamino-1-azetidinyl)-7-fluoro-4-oxo-1,4-dihydrobenzo[b][1,8]naphthyridine-3-carboxylic acid is obtained in the form of yellow solid, melting point 264° C.

1-Cyclopropyl-8-(3-dimethylamino-1 -azetidinyl)-3-ethoxycarbonyl-7-fluoro-4-oxo-1,4 -dihydrobenzo[b][1,8] naphthyridine was prepared under the conditions described in Example 4, but starting with 1.4 g of 1-cyclopropyl-3-ethoxycarbonyl-7,8-difluoro-4-oxo-1,4-dihydrobenzo[b][1, 8]naphthyridine and 1.04 g of 3-(dimethylamino)azetidine dihydrochloride. After concentration of the combined organic extracts to dryness, the solid obtained is recrystallized in 40 cm³ of ethanol. 1.2 g of 1-cyclopropyl-8-(3-dimethylamino-1-azetidinyl)-3-ethoxycarbonyl-7-fluoro-4-oxo-1,4-dihydrobenzo[b][1,8]naphthyridine are obtained in the form of a yellow solid, melting point 225° C.

Example 7

8-(3-Amino-1-azetidinyl)-1-cyclopropyl-7,9-difluoro-4-oxo-1,4-dihydrobenzo[b][1,8]naphthyridine-3-carboxylic acid The reaction is performed under the conditions described in Example 2, but starting with 0.8 g of 8-(3-amino-1-azetidinyl)-1-cyclopropyl-3-ethoxycarbonyl-7,9-difluoro-4-oxo-1,4-dihydrobenzo[b][1,8]naphthyridine. Without recrystallization, 0.6 g of 8-(3-amino-1-azetidinyl)-1-cyclopropyl-7,9-difluoro-4-oxo-1,4-dihydrobenzo[b][1,8]naphthyridine-3-carboxylic acid monohydrate is obtained in the form of a yellow solid, which decomposes at 308°–312° C.

8-(3-Amino-1-azetidinyl)-1-cyclopropyl-3-ethoxycarbonyl-7,9-difluoro-4-oxo-1,4-dihydrobenzo[b][1,8]naphthyridine was prepared under the conditions of Example 2, but starting with 1.3 g of 1-cyclopropyl-3-ethoxycarbonyl-7,8,9-trifluoro-4-oxo-1,4-dihydrobenzo[b][1,8]naphthyridine and 1.32 g of 3-aminoazetidine dimethanesulphonate. After recrystallization in 50 cm³ of ethanol, 0.8 g of 8-(3-amino-1-azetidinyl)-1-cyclopropyl-3-ethoxycarbonyl-7,9-difluoro-4-oxo-1,4-dihydrobenzo[b][1,8]naphthyridine is obtained in the form of a yellow solid, melting point 236°–238° C.

1-Cyclopropyl-3-ethoxycarbonyl-7,8,9-tri-fluoro-4-oxo-1,4-dihydrobenzo[b][1,8]naphthyridine was prepared as described in U.S. Pat. No. 4,970,213.

Example 8

8-(3-Diethylamino-1-azetidinyl)-7-fluoro-4-oxo-1-methyl-1,4-dihydrobenzo[b][1,8]naphthyridine-3-carboxylic acid was prepared under the conditions of Example 2, but starting with 1.75 g of 8-(3-diethylamino-1-azetidinyl)-3-ethoxycarbonyl-7-fluoro-1-methyl-4-oxo-1,4-dihydrobenzo[b][1,8]naphthyridine. 1.4 g of 8-(3-diethylamino-1-azetidinyl)-7-fluoro-4-oxo-1-methyl-1,4-dihydrobenzo[b][1,8]naphthyridine-3-carboxylic acid are obtained in the form of a yellow solid, which decomposes at 297° C.

8-(3-Diethylamino-1-azetidinyl)-3-ethoxy-carbonyl-7-fluoro-1-methyl-4-oxo-1,4-dihydrobenzo[b][1,8]naphthyridine was prepared under the conditions of Example 2, but starting with 2 g of 3-ethoxy-carbonyl-7,8-difluoro-1-methyl-4-oxo-1,4-dihydro-benzo[b][1,8]naphthyridine and 1.4 g of 3-(diethylamino)-azetidine dihydrochloride. After recrystallization of the crude product in 500 cm³ of methanol, 2.07 g of 8-(3-diethylamino-1-azetidinyl)-3-ethoxy-carbonyl-7-fluoro-1-methyl-4-oxo-1,4-dihydrobenzo[b][1,8]naphthyridine are obtained in the form of a yellow solid, melting point 260° C.

3-(Diethylamino)azetidine was prepared in the form of dihydrochloride, melting point 175° C., according to the method described in Japanese Patent Application 74/109,369.

Example 9

8-(3-Ethylamino-1-azetidinyl)-7-fluoro-1-methyl-4-oxo-1,4-dihydrobenzo[b][1,8]naphthyridine-3-carboxylic acid The reaction is performed under the conditions described in Example 2, but starting with 0.51 g of 3-ethoxycarbonyl-8-(3-ethylamino-1-azetidinyl)-7-fluoro-1-methyl-4-oxo-1,4-dihydrobenzo[b][1,8]naphthyridine. 0.4 g of 8-(3-ethylamino-1-azetidinyl)-7-fluoro-1-methyl-4-oxo-1,4-dihydrobenzo[b][1,8]naphthyridine-3-carboxylic acid monohydrate is obtained in the form of a yellow solid, which decomposes at 270° C.

3-Ethoxycarbonyl-8-(3-ethylamino-1-azetidinyl)-7-fluoro-1-methyl-4-oxo-1,4-dihydrobenzo[b][1,8]naphthyridine was prepared under the conditions of Example 2, but starting with 2 g of 7,8-difluoro-3-ethoxycarbonyl-1-methyl-4-oxo-1,4-dihydrobenzo[b][1,8]naphthyridine and 1.3 g of 3-(ethyl-amino)azetidine dihydrochloride. After the addition of 300 cm³ of water to the reaction mixture, the suspension obtained is extracted with 3 times 100 cm³ of dichloromethane. The combined organic extracts are dried over magnesium sulphate and concentrated to dryness under reduced pressure (20 kPa) at a temperature in the region of 40° C. The product obtained is purified by chromatography on 0,063–0,200 mm silica gel suspended in dichloromethane containing 1% of methanol. The desired product is eluted with 500 cm³ of dichloromethane containing 5% of methanol. 0.51 g of 3-ethoxycarbonyl-8-(3-ethyl-amino-1-azetidinyl)-7-fluoro-1-methyl-4-oxo-1,4dihydrobenzo[b][1,8]naphthyridine is obtained in the form of a yellow solid, which decomposes at 215° C. and which is used without further purification for the subsequent steps.

3-(Ethylamino)azetidine dihydrochloride may be prepared by a method analogous to that described by Dino Nisato et al., J. Met. Chem., 22, 961 (1985):

4 g of 1-benzhydryl-3-(ethylamino)azetidine dihydrochloride in 50 cm³ of methanol are hydrogenated at atmospheric pressure and at a temperature in the region of 20° C. for 1 hour in the presence of 800 mg of 20% palladium hydroxide on carbon. After removal of the catalyst by filtration and concentration to dryness under reduced pressure (20 kPa) at approximately 40° C., the residue is taken up with 30 cm³ of ethyl ether, drained and washed with 3 times 20 cm³ of the same solvent. 2.05 g of 3-(ethylumino)azetidine dihydrochloride are obtained in the form of a colorless solid, melting point 200° C. which is used without further purification for the subsequent steps.

1-Benzhydryl-3-(ethylamino)azetidine dihydrochloride is prepared in the following manner:

A mixture of 55 g of 1-benzhydryl-3-(methanesulphonyloxy)azetidine and 70 g of ethylamine in 400 cm³ of methanol is heated to approximately 60° C. for 16 hours. The reaction mixture is then concentrated to dryness under reduced pressure (20 kPa) at approximately 40° C. and the residue is taken up with 200 cm³ of ethyl ether. The organic phase, washed with 90 cm³ of 2N aqueous sodium hydroxide and 3 times 30 cm³ of water, is dried over sodium sulphate and concentrated to dryness under reduced pressure (20 kPa) at approximately 40° C. 22.6 cm³ of 12N hydrochloric acid are added to the dry extract obtained, and the mixture is again concentrated to dryness under the above conditions but at approximately 70° C. The residue is taken up with 100 cm³ of ethyl acetate and 200 cm³ of acetone and drained. 41.4 g of 1-benzhydryl-3-(ethylamino)azetidine dihydrochloride are obtained in the form of a colorless solid, melting point 180° C., which is used without further purification for the subsequent steps.

1-Benzhydryl-3-(methanesulphonyloxy)azetidine was prepared according to the method described by A. G. Anderson et al., J. Org. Chem., 37, 3953 (1972).

Example 10

8-(3-Amino-1-azetidinyl)-7-fluoro-1-methylamino-4-oxo-1,4-dihydrobenzo[b][1,8]naphthyridine-3-carboxylic acid:

A suspension of 1.8 g of 8-(3-acetylamino-1-azetidinyl)-3-ethoxycarbonyl-7-fluoro-1-(N-formyl-N-methylamino)-4-oxo- 1,4-dihydrobenzo[b][1,8]-naphthyridine in 40 cm$^3$ of N aqueous potassium hydroxide is heated with stirring to a temperature in the region of 100° C. for 24 hours. After cooling to approximately 70° C., some slight insoluble matter is removed by filtration. At the same temperature, 40 cm$^3$ of N methanesulphonic acid are added to the filtrate, and the precipitate formed is drained and washed with 3 times 20 cm$^3$ of water at approximately 70° C. After recrystallization in 100 cm$^3$ of dimethylformamide, 1.05 g of 8-(3-amino-1-azetidinyl)-7-fluoro-1-methylamino-4-oxo-1,4-dihydrobenzo[b][1,8 ]naphthyridine-3-carboxylic acid are obtained in the form of a yellow solid, which decomposes at 315°–318° C.

8-(3-Acetylamino-1-azetidinyl)-3-ethoxy-carbonyl-7-fluoro-1-(N-formyl-N-methylamino)-4-oxo-1,4 -dihydrobenzo[b][1,8]naphthyridine was prepared in the following manner:

1.8 g of 7,8-difluoro-3-ethoxycarbonyl-1-(N-formyl-N-methylamino)-4-oxo-1,4-dihydrobenzo[b][1,8 ]naphthyridine are added to a mixture at approximately 30° C. of 1.13 g of 3-(acetylamino)azetidine hydrochloride and 0.85 g of sodium carbonate in 40 cm$^3$ of dimethyl sulphoxide, and the mixture is heated to approximately 80° C. for 2 hours. After cooling to approximately 20° C., the reaction mixture is poured into 100 cm$^3$ of water at approximately 5° C. The precipitate is drained and washed with 3 times 50 cm$^3$ of water. 2.05 g of 8-(3-acetyl-amino-1-azetidinyl)- 3-ethoxycarbonyl-7-fluoro-1-(N-formyl-N-methylamino)-4-oxo-1,4-dihydrobenzo[b][1,8]naphthyridine are obtained in the form of a yellow solid, which decomposes at 305° C.

7,8-Difluoro-3-ethoxycarbonyl-1-(N-formyl-N-methylamino)-4-oxo-1,4-dihydrobenzo[b][1,8]naphthyridine was prepared in the following manner:

A solution of 1.63 g of N-formyl-N-methylhydrazine in 30 cm$^3$ of dichloromethane is added in the course of 10 minutes at approximately 20° C. to a stirred solution of 7.4 g of ethyl 2-(2-chloro-6,7-difluoro-3-quinolinecarbonyl)-3-(dimethylamino)-acrylate in 30 cm$^3$ of dichloromethane. After 16 hours at a temperature in the region of 20° C., the reaction mixture is concentrated under reduced pressure (20 kPa) at approximately 40° C. The dry extract is taken up with 100 cm$^3$ of ethanol and 3 cm$^3$ of 1,8-diazabicyclo[5.4.0 ]-undec-7-ene (DBU) and heated to approximately 75° C. for 30 minutes After cooling to approximately 20° C., the product is drained and washed with twice 50 cm$^3$ of ethanol and twice 30 cm$^3$ of ethyl ether. 3.9 g of 7,8-difluoro-3-ethoxy-carbonyl-1-(N-formyl-N-methylamino)-4-oxo-1,4-dihydro-benzo[b][1,8]naphthyridine are obtained in the form of a yellow solid, melting point 259–260° C., which is used without further purification for the subsequent steps.

Ethyl 2-(2-chloro-6,7-difluoro-3-quinolinecarbonyl)-3-(dimethylamino)acrylate was prepared as described in U.S. Pat. No. 4,970,213.

3-(Acetylamino)azetidine hydrochloride was prepared according to the method described by Dino Nisato et al., J. Heterocyclic Chem. 22, 961 (1985).

Example 11

8-(trans-3-Amino-2-methyl-1-azetidinyl)-7-fluoro-1-methyl-4-oxo-1,4-dihydrobenzo[b][1,8S] naphthyridine-3-carboxylic acid A solution of 18 g of trans-3-amino-2-methylazetidine dimethanesulphonate and 12.7 g of triethylamine in 150 cm$^3$ of dimethyl sulphoxide is heated with stirring to approximately 70° C. for 20 minutes. At the same temperature, 14.5 g of 7,8-difluoro-1-methyl-4-oxo-1,4-dihydrobenzo[b][1,8 ]naphthyridine-3-carboxylic acid are added in small portions in the course of 10 minutes, and the mixture is heated to approximately 90° C. for 2 hours. After cooling to approximately 20° C., the reaction mixture is poured into 400 cm$^3$ of water at the same temperature. The insoluble matter is drained, washed with twice 100 cm$^3$ of water and twice 100 cm$^3$ of ethanol and recrystallized in 300 cm$^3$ of dimethylformamide. 13.9 g of 8-(trans-3-amino-2-methyl-1-azetidinyl)-7-fluoro-1 -methyl-4-oxo-1,4-dihydrobenzo[b][1,8] naphthyridine-3-carboxylic acid are obtained in the form of a yellow solid, which decomposes at 265°–267° C.

trans-3-Amino-2-methylazetidine was prepared in the form of the dimethanesulophonate, m.p. 170°–175° C., according to the synthesis described in Patent Application EP 406,112.

Example 12

-(cis-3-Amino-2-methyl-1-azetidinyl)-7-fluoro-1-methyl-4-oxo-1,4-dihydrobenzo[b][1,8] naphthyridine-3 -carboxylic acid The reaction is performed under the conditions of Example 11, but starting with 1.45 g of 7,8-difluoro-1-methyl-4-oxo-1,4-dihydrobenzo[b][1,8 ]-naphthyridine-3-carboxylic acid and 2.1 g of cis-3 -amino-2-methylazetidine dimethanesulphonate- 1.32 g of 8-(cis-3-amino-2-methyl-1-azetidinyl)-7-fluoro-1 -methyl-4-oxo-1,4-dihydrobenzo[b][1,8]-acid are obtained in the form of yellow solid, which decomposes at 312°–315° C.

cis-3-Amino-2-methylazetidine was prepared in the form of the dimethanesulphonate, melting point 160°–170° C., according to the synthesis described in Patent Application EP 406,112.

Example 13

8-(trans-3-Amino-2-methyl-1-azetidinyl)-1-cyclopropyl-7-fluoro-4-oxo-1,4-dihydrobenzo[b][1,8] naphthyridine-3 -carboxylic acid A suspension of 1.4 g of 8-(trans-3-amino-2-methyl-1-azetidinyl)-1-cyclopropyl-3-ethoxycarbonyl-7-fluoro-4-oxo-1,4-dihydrobenzo[b][1,8]naphthyridine in 15 cm$^3$ of water and 6.8 cm$^3$ of N aqueous potassium hydroxide is heated to approximately 95° C. for 3 hours. After cooling to approximately 60° C., some very slight insoluble matter is removed by filtration; at the same temperature, 6.8 cm$^3$ of N methanesulphonic acid are added to the filtrate. The insoluble matter formed is drained at approximately 20° C.

and washed with 3 times 50 cm³ of water and twice 25 cm³ of ethanol. After recrystallization in 30 cm³ of dimethylformamide, one obtains 1.03 g of 8-(trans-3-amino-2-methyl-1-azetidinyl)-1-cyclopropyl-7-fluoro-4-oxo-1,4-dihydrobenzo[b][1,8]naphthyridine-3-carboxylic acid in the form of a yellow solid, which decomposes at 268°–270° C.

8-(trans-3-Amino-2-methyl-1-azetidinyl)-1- cyclopropyl-3-ethoxycarbonyl-7-fluoro-4-oxo-1,4-dihydrobenzo[b][1,8] naphthyridine was prepared in the following manner:

1.7 g of 1-cyclopropyl-3-ethoxycarbonyl-7,8-difluoro-4-oxo-1,4-dihydrobenzo[b][1,8]-naphthyridine are added in small portions in the course of 10 minutes to a solution of trans-3-amino-2-methylazetidine dimethanesulphonate in 20 cm³ of dimethyl suphoxide and 1.52 g of triethylamine at approximately 60° C. The reaction mixture is heated to a temperature in the region of 80° C., and kept stirring at the same temperature for approximately 4 hours. After cooling to approximately 20° C., the reaction mixture is poured into 100 cm³ of water and extracted with twice 100 cm³ of dichloromethane. The combined organic extracts are washed with twice 50 cm³ of water, dried over magnesium sulphate and concentrated to dryness under reduced pressure (20 kPa) at approximately 40° C. The dry extract is chromatographed on 125 g of silica gel (0.04–0.063 mm) suspended in a dichloromethane mixture containing 20% of ethanol. The desired product is eluted with 300 cm³ of the same mixture. 1.6 g of 8-(trans-3-amino-2-methyl-1-azetidinyl)-1-cyclopropyl-3-ethoxycarbonyl-7-fluoro-4-oxo-1,4-dihydrobenzo[b][1,8]naphthyridine-3-carboxylic acid are obtained in the form of a yellow solid, melting point 170° C.

Example 14

8-(3-Amino-1-azetidinyl)-7-fluoro-4-oxo-1-tert-butyl-1,4-dihydrobenzo[b][1,8]naphthyridine-3-carboxylic acid A suspension of 2.2 g of 8-(3-trifluoro-acetamido-1-azetidinyl)-3-ethoxycarbonyl-7-fluoro-4 -oxo-1-tert-butyl-1,4-dihydrobenzo[b][1,8]naphthyridine in 17 cm³ of N aqueous potassium hydroxide is heated to approximately 95° C. for 7 hours. At the same temperature, 17 cm³ of N methanesulphonic acid are added and the product is drained at approximately 90° C., washed with twice 30 cm³ of water and twice 30 cm³ of ethanol and recrystallized in 50 cm³ of dimethylformamide. 1.4 g of 8-(3-amino-1-azetidinyl)-7-fluoro-4-oxo-1-tert-butyl-1,4-dihydrobenzo[b][1,8 ]-naphthyridine-3-carboxylic acid are obtained in the form of a yellow solid, which decomposes at 333°–335° C.

3-Ethoxycarbonyl-7-fluoro-8-(3-trifluoro-acetamido-1-azetidinyl)-4-oxo-1-tert-butyl-1,4-dihydrobenzo[b][1,8] naphthyridine was prepared under the conditions described in Example 2, but starting with with 1.8 g of 3-ethoxycarbonyl-7,8-difluoro-4-oxo-1 -tert-butyl-1,4-dihydrobenzo[b][1,8]naphthyridine, 1.5 g of 3-(trifluoroacetamido)azetidine hydrochloride and 0.79 g of sodium carbonate. 2.25 g of 3-(ethoxycarbonyl-7-fluoro-8-(3-trifluoroacetamido-1-azetidinyl)-4-oxo-1-tert-butyl-1,4-dihydrobenzo[b][1,8]naphthyridine are obtained in the form of a yellow solid, melting point 328°–330° C.

3-Ethoxycarbonyl-7,8-difluoro-4-oxo-1-tert-butyl-1,4-dihydrobenzo[b][1,8]naphthyridine was prepared under the conditions described in Example 10, but starting with 4 g of ethyl 2-(2-chloro-6,7-difluoro-3-quinolylcarbonyl)-3(dimethylamino)acrylate and 0.87 g of tert-butylamine. 2.7 g of 3-ethoxycarbonyl-7,8-difluoro-4-oxo-1-tert-butyl-1,4dihydrobenzo[b][1,8]naphthyridine are obtained in the form of a yellow solid, melting point 206° C., which is used without further purification for the subsequent steps.

3-(Trifluoroacetamido)azetidine hydrochloride was prepared as described in Patent Application EP 406,112.

Example 15

8-(3-Amino-3-propyl-1-azetidinyl)-7-fluoro-1-methyl-4
-oxo-1,4-dihydrobenzo[b][1,8]naphthyridine-3-carboxylic acid 2.3 g of 3-amino-3-propylazetidine dimethanesulphonate are added to a solution of 1.22 g of sodium ethylate in 18 cm³ of ethanol. After the addition of 30 cm³ of dimethyl sulphoxide, the solution is stirred for 10 minutes at approximately 20° C. At the same temperature, 1.45 g of 7,8-difluoro-1-methyl-4-oxo-1,4-dihydrobenzo[b][1,8]naphthyridine-3-acid are added and the mixture is heated with stirring to approximately 90° C. for 5 hours. After cooling to approximately 20° C., the product is drained and washed with 4 times 20 cm³ of water and twice 10 cm³ of ethanol. After recrystallization in 30 cm³ of dimethylformamide, 1.52 g of 8-(3-amino-3-propyl-1-azetidinyl)-7-fluoro-1-methyl-4-oxo-1,4-dihydrobenzo[b][1,8]naphthyridine-3-carboxylic acid are obtained in the form of a yellow solid, which decomposes at 304°–305° C.

3-Amino-3-propylazetidine in the form of the dimethanesulphonate was prepared under conditions similar to those described by D. Nisato et al., J. Heterocyclic, 22, 961 (1985).

By hydrogenation of 7.3 g of 3-amino-1-benzhydryl-3-propylazetidine at a pressure of 1 atmosphere in the presence of 5 g of methanesulphonic acid in 75 cm³ of methanol and 1.5 g of 20% palladium hydroxide on carbon, 6.5 g of 3-amino-3-propylazetidine dimethanesulphonate are obtained. The product is taken up in ethanol and isolated in the form of a colorless solid, melting point 200° C.

3-Amino-1-benzhydryl-3-propylazetidine was prepared in the following manner:

7.5 g of 1-benzhydryl-3-methanesulphonyloxy-3-propylazetidine are added to a solution at approximately 5° C. of 100 cm³ of a solution of ammonia in ethanol (prepared from 15 g of ammonia in 100 cm³ of ethanol at 5° C., the temperature is allowed to rise to approximately 20° C. and the mixture is stirred for 16 hours at the same temperature. After concentration to dryness under reduced pressure (20 kPa) at approximately 40° C., the residue is taken up with 25 cm³ of water and 2.22 g of methanesulphonic acid. The aqueous phase is washed with twice 25 cm³ of ethyl ether, treated with 10 cm³ of 40% aqueous sodium hydroxide and extracted with 3 times 50 cm³ of dichloromethane; the combined organic extracts are washed with 10 cm³ of water saturated with sodium chloride, dried over magnesium sulphate and concentrated to dryness under the above conditions. 5.2 g of 3-amino-1-benzhydryl-3-propylazetidine are obtained in the form of an oily product, which is used without further purification for the subsequent steps.

1-Benzhydryl-3-methanesulphonyloxy-3-propylazetidine was prepared under the conditions described for 1-benzhydryl-3-methanesulphonyloxy-3-methylazetidine in Patent Application EP 406,112, but starting with 2.4 g of 1-benzhydryl-3-hydroxy-3-propylazetidine. 2.4 g of 1-Benzhydryl-3-methanesulphonyloxy-3-propylazetidine are obtained in the form of a colorless solid, melting point 70° C.

1-Benzhydryl-3-hydroxy-3-propylazetidine was prepared under the following conditions:

A solution of 7.5 g of 1-benzhydryl-3-oxoazetidine dissolved in 50 cm³ of ethyl ether is added in the course of 20 minutes at between 0 and 5° C. to a solution of propylmagnesium iodide in ethyl ether, prepared under the usual conditions from 10.75 g of iodopropane and 1.55 g of magnesium in 75 cm³ of ethyl ether. The temperature is allowed to rise to approximately 20° C. and the mixture is stirred at the same temperature for 2 hours. After cooling to approximately 0° C., 50 cm³ of water and 50 cm³ of 10% aqueous ammonium chloride solution are added successively while the latter temperature is maintained. The aqueous phase is extracted with 3 times 50 cm³ of ethyl ether. The combined organic extracts are dried over magnesium sulphate and concentrated to dryness under reduced pressure (20 kPa) at approximately 30° C. The dry extract is chromatographed on 100 g of silica gel (0.04–0.063 mm) suspended in a cyclohexane mixture containing 20% of ethyl acetate. The desired product is eluted with 130 cm³ of the same solvent mixture. 8 g of 1-benzhydryl-3-hydroxy-3-propyl-azetidine are obtained in the form of a pale yellow oil, which is used without further purification for the subsequent steps.

1-Benzhydryl-3-oxo-azetidine was prepared under the conditions described by A. Morimoto et al. Chem. Pharm. Bull. 21 (1) 228–231 (1973).

Example 16

8-(3-Amino-3-methyl-1-azetidinyl)-7-fluoro-1-methyl-4-oxo-1,4-dihydrobenzo[b][1,8]naphthyridine-3-carboxylic acid 2.09 g of 3-amino-3-methylazetidine dimethanesulphonate are added to a solution of 1.02 g of sodium ethylate in 30 cm³ of ethanol at approximately 5° C. The temperature is allowed to rise to approximately 20° C. and the mixture is stirred for 15 minutes at the same temperature. After removal of inorganic salts by filtration, the filtrate is concentrated to dryness under reduced pressure (20 kPa) at approximately 30° C. The residue is dissolved in 20 cm³ of dimethyl sulphoxide is treated at a temperature in the region of 20° C. with 1.45 g of 7,8-difluoro-1-ethyl-4-oxo-1,4-dihydrobenzo[b][1,8]naphthyridine-3-carboxylic acid. The suspension obtained is stirred for 16 hours at the same temperature and then heated to approximately 60° C. for 1 hour. After cooling to approximately 20° C., the insoluble matter is drained and washed with 30 cm³ of ethanol. The product isolated is recrystallized in 90 cm³ of dimethylformamide, drained and washed with 20 cm³ of ethanol at approximately 75° C. 1.2 g of 8-(3-amino-3-methyl-1-azetidinyl)-7-fluoro-1-methyl-4-oxo-1,4-dihydrobenzo[b][1,8]naphthyridine-3-carboxylic acid are obtained in the form of a yellow solid, which decomposes at 345° C.

3-Amino-3-methylazetidine in the form of the dimethanesulphonate, melting point 204°–206° C., is prepared under the conditions described in Patent Application EP 406,112.

Example 17

8-(3-Amino-3-methyl-1-azetidinyl)-1-ethyl-7-fluoro-4-oxo-1,4-dihydrobenzo[b][1,8]naphthyridine-3-carboxylic acid was prepared in the conditions described in Example 15, but starting with 1.52 g of 7,8-difluoro-1-ethyl-4-oxo-1,4-dihydrobenzo[b][1,8]-naphthyridine-3-carboxylic acid and 2.22 g of 3-amino-3-methylazetidine dimethanesulphonate, for 72 hours at approximately 20° C. and then 1 and a half hours at a temperature in the region of 90° C. The insoluble matter in the reaction mixture is drained at approximately 20° C., washed with twice 20 cm³ of water, recrystallized in 70 cm³ of dimethylformamide and washed with 40 cm³ of ethanol at approximately 75° C. 1.45 g of 8-(3-Amino-3-methyl-1-azetidinyl)-1-ethyl-7-fluoro-4-oxo-1,4-dihydrobenzo[b][1,8]naphthyridine-3-carboxylic acid are obtained in the form of a yellow solid, which decomposes at 334° C.

Example 18

8-(3-Amino-3-methyl-1-azetidinyl)-1-cyclopropyl-7-fluoro-4-oxo-1,4-dihydrobenzo[b][1,8]-naphthyridine-3-carboxylic acid was prepared under the conditions described in Example 16, but starting with 1.58 g of 1-cyclopropyl-7,8-difluoro-4-oxo-1,4-dihydrobenzo[b][1,8]naphthyridine-3-carboxylic acid and 2.22 g of 3-amino-3-methylazetidine dimethanesulphonate. 1.7 g of 8-(3-amino-3-methyl-1-azetidinyl)-1-cyclopropyl-7-fluoro-4-oxo-1,4-dihydrobenzo[b][1,8]naphthyridine-3-carboxylic acid are obtained in the form of a yellow solid, which decomposes at 298° C.

1-Cyclopropyl-7,8-difluoro-4-oxo-1,4-dihydrobenzo[b][1,8]naphthyridine-3-carboxylic acid was prepared under the following conditions:

A suspension of 8.05 g of 1-cyclopropyl-3-ethoxy-carbonyl-7,8-difluoro-4-oxo-1,4-dihydrobenzo-[[b][1,8]naphthyridine in a mixture of 80 cm³ of 17.5% aqueous hydrochloric acid solution and 80 cm³ of acetic acid is heated with stirring to a temperature in the region of 100° C. for 2 hours. After cooling to approximately 20° C., the product is drained and washed with 3 times 100 cm³ of water. 6.25 g of 1-cyclopropyl-7,8-difluoro-4-oxo-1,4-dihydrobenzo[b][1,8]-naphthyridine-3-carboxylic acid are obtained in the form of a pale yellow solid, which decomposes at 238° C. and which is used without further purification for the subsequent steps.

Example 19

(RS)-8-(3-Amino-2,2-dimethyl-1-azetidinyl)-7-fluoro-1-methyl-4-oxo-1,4-dihydrobenzo[b][1,8]-naphthyridine-3-carboxylic acid was prepared under the conditions described in Example 15, but starting with 1.45 g of 7,8-difluoro-1-methyl-4-oxo-1,4-dihydrobenzo-[b][1,8]naphthyridine-3-carboxylic acid and 2.33 g of 3-amino-2,2-dimethylazetidine dimethanesulphonate. The reaction mixture is heated with stirring to approximately 100° C. for 5 hours. 0.6 g of (RS)-8-(3-amino-2,2-dimethyl-1-azetidinyl)-7-fluoro-1-methyl-4-oxo-1,4-dihydrobenzo[b][1,8]naphthyridine-3-carboxylic acid is obtained in the form of a yellow solid, which decomposes at 285° C.

3-Amino-2,2-dimethylazetidine dimethanesulphonate was prepared in the form of a white solid, melting point 125°–130° C. from 3-amino-2,2,dimethylazetidine, by adaptation of the method described by Akira Morimoto Chem. Pharm. Bull., 21 (1), 228 (1973).

Example 20

7-Fluoro-1-methyl-8-(3-methyl-3-methylamino-1-azetidinyl)-4-oxo-1,4-dihydrobenzo[b][1,8]-naphthyridine-3-carboxylic acid was prepared under the conditions of Example 15, but starting with 1.45 g of 7,8-difluoro-1- methyl-4-oxo-1,4-dihydrobenzo[b]-[1,8]naphthyridine-3-carboxylic acid and 2.34 g of 3-methyl-3-(methylamino)azetidine dimethanesulphonate. The reaction mixture is heated for 1 and a half hours to approximately 90° C. 1.12 g of 7-fluoro-1-methyl-8-(3-methyl-3-methylamino-1-azetidinyl)-1-methyl-4-oxo-1,4-dihydrobenzo[b][1,8]naphthyridine-3-carboxylic acid are obtained in the form of a yellow solid, which decomposes at approximately 336° C.

3-Methyl-3-(methylamino)azetidine in the form of the dimethanesulphonate (melting point 135°) was prepared under the conditions described in Patent Application EP 406,112.

Example 21

1-Cyclopropyl-7-fluoro-8-(3-methyl-3 -methylamino-1-azetidinyl)-4-oxo-1,4 -dihydrobenzo[b][1,8]naphthyridine-3-carboxylic acid was prepared under the conditions of Example 15, but starting with 1.58 g of 7,8-difluoro-1-cyclopropyl-4-oxo-1,4-dihydrobenzo[b][1,8]naphthyridine-3-carboxylic acid and 2.34 g of 3-methyl-3-(methylamino)azetidine dimethanesulphonate. 1.57 g of 1-cyclopropyl-7-fluoro-8-(3-methyl-3-methylamino-1-azetidinyl)-4-oxo-1,4-dihydrobenzo[b][1,8]naphthyridine-3-carboxylic acid are obtained in the form of a yellow solid, which decomposes at 330° C.

Example 22

1-Ethyl-7-fluoro-8-(3-methyl-3-methylamino-1-azetidinyl)-4-oxo-1,4-dihydrobenzo[b][1,8 ]-naphthyridine-3-carboxylic acid was prepared under the conditions of Example 15, but starting with 1.52 g of 7,8-difluoro-1-ethyl-4-oxo-1,4-dihydrobenzo[b]-[1,8]naphthyridine-3-carboxylic acid and 2.34 g of 3-methyl-3-(methylamino)azetidine dimethanesulphonate. 1.18 g of 1-ethyl-7-fluoro-8-(3-methyl-3-methylamino-1 -azetidinyl)-4-oxo-1,4-dihydrobenzo[b][1,8 ]-naphthyridine-3-carboxylic acid are obtained in the form of a yellow solid, which decomposes at 338° C.

Example 23

8-(3-Amino-3-methyl-1-azetidinyl)-7-fluoro-1 -methoxy-4-oxo-1,4-dihydrobenzo[b][1,8]naphthyridine-3carboxylic acid was prepared under the conditions of Example 15, but starting with 1.53 g of 7,8-difluoro-1 -methoxy-4-oxo-1,4-dihydrobenzo[b][1,8]naphthyridine-3carboxylic acid and 2.22 g of 3-amino-3-methylazetidine dimethane-sulphonate. 1.27 g of 8-(3-amino-3-methyl-1-azetidinyl)-7-fluoro-1-methoxy-4-oxo-1,4-dihydrobenzo[b][1,8]naphthyridine-3-carboxylic acid are obtained in the form of a yellow solid, which decomposes at 346° C.

7,8-Difluoro-1-methoxy-4-oxo-1,4 -dihydrobenzo[b][1,8S]naphthyridine-3-carboxylic acid is prepared under the conditions described in U.S. Pat. No. 4,970,213.

Example 24

1-Cyclopropyl-7-fluoro-8-(3-methyl-3-dimethylamino-1-azetidinyl)-4-oxo-1,4 -dihydrobenzo[b][1,8]naphthyridine-3-carboxylic acid was prepared under the conditions of Example 15, but starting with 1.58 g of 1-cyclopropyl-7,8-difluoro-4-oxo-1,4-dihydrobenzo[b][1,8]naphthyridine-3-carboxylic acid and 2.45 g of 3-methyl-3-(dimethylamino)azetidine dimethanesulphonate. 1.55 g of 1-cyclopropyl-7-fluoro-8-(3-methyl-3-dimethylamino-1-azetidinyl)-4-oxo-1,4-dihydrobenzo[b][1,8 ]-naphthyridine-3-carboxylic acid are obtained in the form of a yellow solid, which decomposes at 268° C.

3-Methyl-3-(dimethylamino)azetidine in the form of the dimethanesulphonate, melting point 148° C., is prepared under the conditions described in Patent Application EP 406,112.

Example 25

7-Fluoro-1-methyl-8-(3-methyl-3 -dimethylamino-1-azetidinyl)-4-oxo-1,4 -dihydrobenzo[b][1,8]naphthyridine-3-carboxylic acid was prepared under the conditions described in Example 15, but starting with 1.45 g of 7,8-difluoro-1-methyl-4-oxo-1,4-dihydrobenzo[b][1,8]naphthyridine-3-carboxylic acid and 2.45 g of 3-methyl-3-(dimethylamino)azetidine dimethanesulphonate. 1.56 g of 7-fluoro-1-methyl-8-(3-methyl-3-dimethylamino-1-azetidinyl)-4-oxo-1,4-dihydrobenzo[b][1,8]naphthyridine-3-carboxylic acid are obtained in the form of a yellow solid, which decomposes at 274° C.

Example 26

8-(3-Amino-3-methyl-1-azetidinyl)-7,9 -difluoro-1-methyl-4-oxo-1,4-dihydrobenzo[b][1,8 ]-naphthyridine-3-carboxylic acid was prepared under the following conditions:

1.33 g of 3-amino-3-methylazetidine dimethanesulphonate are added to a solution of 0.68 g of sodium ethylate in 7 cm$^3$ of ethanol. After the addition of 20 cm$^3$ of dimethyl sulphoxide, the solution is stirred for 10 minutes at approximately 20° C. At the same temperature, 0.75 g of 7,8,9-trifluoro-1-methyl-4-oxo-1,4-dihydrobenzo[b][1,8]naphthyridine-3-carboxylic acid is added, and the mixture is stirred for 72 hours at approximately 20° C.

The insoluble matter is drained and washed with twice 20 cm$^3$ of water and twice 20 cm$^3$ of ethanol. After recrystallization in 70 cm$^3$ of dimethylformamide, 0.45 g of 8-(3-amino-3-methyl-1-azetidinyl)-7,9-difluoro-1-methyl-4-oxo-1,4-dihydrobenzo[b][1,8 ]-naphthyridine-3-carboxylic acid is obtained in the form of a yellow solid, which decomposes at 359° C.

7,8,9-Trifluoro-1-methyl-4-oxo-1,4 -dihydrobenzo[b][1,8]naphthyridine-3-carboxylic acid was prepared in the following manner:

A suspension of 0.88 g of 3-ethoxycarbonyl-7,8,9-trifluoro-1-methyl-4-oxo-1,4 -dihydrobenzo-[b][1,8]naphthyridine in a mixture of 10 cm$^3$ of 17.5% aqueous hydrochloric acid solution and 10 cm$^3$ of acetic acid is heated with stirring to a temperature in the region of 100° C. for 3 hours. After cooling to approximately 20° C., the product is drained and washed with 3 times 10 cm$^3$ of water. 0.75 g of 7,8,9-trifluoro-1-methyl-4-oxo-1,4-dihydrobenzo[b][1,8]naphthyridine-3carboxylic acid is obtained in the form of a pale yellow solid, which decomposes at 352° C. and which is used without further purification for the subsequent steps.

3-Ethoxycarbonyl-7,8,9-trifluoro-1-methyl-4 -oxo-1,4-dihydrobenzo[b][1,8]naphthyridine was prepared under the conditions described in U.S. Pat. No. 4,970,213.

Example 27

8-(3-Cyclopropylamino-3-methyl-1-azetidinyl)-7-fluoro-1-methyl-4-oxo-1,4-dihydrobenzo[b][1,8 ]-naphthyridine-3-carboxylic acid was prepared under the conditions of Example 15, but starting with 1.45 g of 7,8-difluoro-1-methyl-4-oxo-1,4 -dihydrobenzo[b][1,8]naphthyridine-3-carboxylic acid and 2.5 g 3-cyclopropylamino-3-methylazetidine dimethanesulphonate. 1.73 g of 8-(3- cyclopropylamino-3-methyl-1-azetidinyl)-7-fluoro-1-methyl-4-oxo-1,4 -dihydrobenzo[b][1,8]naphthyridine-3-carboxylic acid, solvated with 0.7% of water is obtained in the form of a yellow solid, which decomposes at 300° C.

3-Cyclopropylamino-3-methylazetidine dimethanesulphonate was prepared in the following manner:

14.5 g of 1-benzhydryl-3-cyclopropylamino-3-methylazetidine in 150 cm³ of methanol are hydrogenated at atmospheric pressure and at a temperature in the region of 20° C. for 1 hour in the presence of 5.6 g of 20% palladium hydroxide on carbon. The reaction mixture is treated with 10 g of methanesulphonic acid. After removal of the catalyst by filtration and concentration to dryness under reduced pressure (20 kPa) at approximately 40° C., the residue is washed with 3 times 150 cm³ of ethyl ether. The final residue is taken up with 100 cm³ of 2-propanol, drained and washed with twice 50 cm³ of acetone. 9.1 g of 3-cyclopropylamino-3-methylazetidine dimethanesulphonate are obtained in the form of a colorless solid, melting point 136° C.

1-Benzhydryl-3-cyclopropylamino-3-methylazetidine was prepared in the following manner:

A suspension of 16.6 g of 1-benzhydryl-3-methane-sulphonyloxy-3-methylazetidine and 28.84 g of of cyclopropylamine in 250 cm³ of ethanol is stirred for 96 hours at approximately 20° C. The reaction mixture is concentrated under reduced pressure (20 kPa) at approximately 30° C. The dry extract is taken up with 50 cm³ of water and 8.8 g of methanesulphonic acid. The aqueous phase is washed with 3 times 25 cm³ of dichloromethane, treated with 12 cm³ of 35% aqueous sodium hydroxide and extracted with 3 times 50 cm³ of ethyl acetate. The combined organic phases are washed with twice 50 cm³ of water, dried over magnesium sulphate and concentrated to dryness under reduced pressure (20 kPa) at approximately 25° C. 14.6 g of 1-benzhydryl-3-cyclopropylamino-3-methylazetidine are obtained in the form of a yellow oil, which is used without further purification for the subsequent steps.

1-Benzhydryl-3-methanesulphonyloxy-3-methylazetidine was prepared according to the conditions described in Patent Application EP 406,112.

Example 28

8-(3-Ethylamino-3-methyl-1-azetidinyl)-7 -fluoro-1-methyl-4-oxo-1,4-dihydrobenzo[b][1,8 ]-naphthyridine-3-carboxylic acid was prepared under the conditions of Example 15, but starting with 1.45 g of 7,8-difluoro-1-methyl-4-oxo-1,4 -dihydrobenzob[b][1,8]naphthyridine-3-carboxylic acid and 2.24 g of -ethylamino-3-methylazetidine dimethanesulphonate. 1.66 g of 8-(3-Ethylamino-3-methyl-1-azetidinyl)-7 -fluoro-1-methyl-4-oxo-1,4-dihydrobenzo[b][1,8] -naphthyridine-3-carboxylic acid are obtained in the form of a yellow solid, which decomposes at 312° C.

3-Ethylamino-3-methylazetidine dimethanesulphonate was prepared under the conditions described in Example 27, but starting with 14 g of 1-benzhydryl-3-ethyl-amino-3-methylazetidine. 9.7 g of 3-ethylamino-3-methyl-azetidine dimethanesulphonate are obtained in the form of a colorlese solid, melting point 140° C.

1-Benzhydryl-3-ethylamino-3-methylazetidine was prepared under the conditions described in Example 27, but starting with 16.6 g of 1-benzhydryl-3 -methanesulphonyloxy-3-methylazetidine and 45 g of ethylamine. 14 g of 1-benzhydryl-3-ethylamino-3-methylazetidine are obtained in the form of a yellow oil, which is used without further purification for the subsequent steps.

Example 29

7-Fluoro-8-(3-methylamino-1-azetidinyl)-1 -methoxy-4-oxo-1,4-dihydrobenzo[b][1,8]naphthyridine-3-carboxylic acid was prepared under the conditions of Example 2, but starting with 2.6 g of 3-ethoxycarbonyl-7-fluoro-1-methoxy-8-(3-methylamino-1-azetidinyl)-4 -oxo-1,4-dihydrobenzo[b][1,8]naphthyridine. 1.7 g of 7-fluoro-8-(3-methylamino-1-azetidinyl)-1-methoxy-4-oxo-1,4-dihydrobenzo[b][1,8]naphthyridine-3-carboxylic acid are obtained in the form of a yellow solid, which decomposes at 255°–260° C.

3-Ethoxycarbonyl-7-fluoro-1-methoxy-8-(3 -methylamino-1-azetidinyl)-4-oxo-1,4 -dihydrobenzo[b][1,8]naphthyridine was prepared under the following conditions:

2.8 g of 3-(methylamino)azetidine dihydrochloride are added to a solution of 2.36 g of sodium ethylate in 20 cm³ of ethanol. After 15 minutes' stirring at a temperature in the region of 20° C. and removal of the inorganic salts by filtration, the filtrate is concentrated to dryness under reduced pressure (20 kPa) at approximately 30° C. The residue is dissolved in 40 cm³ of dimethylsulphoxide and the solution treated with 2.7 g of 3-ethoxycarbonyl-7,8-difluoro-1-methoxy-4-oxo-1,4-dihydrobenzo[b][1,8]-naphthyridine. The reaction mixture is heated to approximately 60° C. for 1 and a half hours. 2.7 g of 3 -ethoxycarbonyl-7-fluoro-8-(3-methylamino-1-azetidinyl)-1-methoxy-4-oxo-1,4-dihydrobenzo[b][1,8]naphthyridine are obtained in the form of a yellow solid, melting point 234° C.

3-(Methylamino)azetidine dihydrochloride was prepared under the conditions described in Example 9, but starting with 32.2 [lacuna] of 1-benzhydryl-3-(methylamino)azetidine. 19.1 g of 3-(methylamino)azetidine dihydrochloride are obtained in the form of a colorless solid, melting point 138°–140° C.

1-Benzhydryl-3-(methylamino)azetidine was prepared under the conditions of Example 9, but starting with 50 g of 1-benzhydryl-3-(methanesulphonyloxy)-azetidine and 48.9 g of methylamine in 250 cm³ of methanol. 27 g of 1-benzhydryl-3-(methylamino)azetidine are obtained in the form of a colorless solid, melting point 75° C.

Example 30

1-Cyclopropyl-7-fluoro-8-(3-methylamino-1-azetidinyl)-4-oxo-1,4-dihydrobenzo[b][1,8 ]-naphthyridine-3-carboxylic acid was prepared under the conditions of Example 11, but starting with 1.5 g of 1-cyclopropyl-7,8-difluoro-4-oxo-1,4 -dihydrobenzo[b][1,8]naphthyridine-3-carboxylic acid and 1.13 g of 3-(methylamino)azetidine dihydrochloride. The reaction mixture is stirred for 1 hour at 40° C. 1 g of 1-cyclopropyl-7-fluoro-8-(3-methylamino-1-azetidinyl)-4-oxo-1,4-dihydrobenzo[b][1,8]naphthyridine-3-carboxylic acid is obtained in the form of a yellow solid, which decomposes at 262° C.

Example 31

7,9-Difluoro-1-methyl-8-(3-methylamino-1-azetidinyl)-4-oxo-1,4-dihydrobenzo[b][1,8 ]-naphthyridine-3-carboxylic acid was prepared under the conditions of Example 30, but starting with 1.5 g of 7,8,9-trifluoro-1-methyl-4-oxo-1,4 -dihydrobenzo[b][1,8]naphthyridine-3-carboxylic acid and 1.2 g of 3-(methylamino)azetidine dihydrochloride. 1.54 g of 7,9-difluoro-1-methyl-8-(3-methylamino-1-azetidinyl)-4-oxo-1,4-dihydrobenzo[b][1,8]naphthyridine-3-carboxylic acid are obtained in the form of a yellow solid, which decomposes at 302° C.

Example 32

8-(3-Amino-3-ethyl-1-azetidinyl)-7-fluoro-1-methyl-4-oxo-1,4-dihydrobenzo[b][1,8]naphthyridine-3carboxylic acid was prepared under the conditions of Example 15, but starting with 1.66 g of 7,8-difluoro-1-methyl-4-oxo-1,4-dihydrobenzo[b][1,8]naphthyridine-3-carboxylic acid and 3.1 g of 3-amino-3-ethylazetidine dimethane-sulphonate. 1.46 g of 8-(3-amino-3-ethyl-1-azetidinyl)-7-fluoro-1-methyl-4-oxo-1,4 -dihydrobenzo[b][1,8]naphthyridine-3-carboxylic acid are obtained in the form of a yellow solid, which decomposes at 294° C.

3-Amino-3-ethylazetidine dimethanesulphonate was prepared according to the conditions described in Example 15 for 3-amino-3-propylazetidine dimethanesulphonate: 5.7 g of 3-amino-3-ethylazetidine dimethanesulphonate were obtained in the form of a colorless solid, melting point 184° C., by hydrogenation of 6 g of 3-amino-1-benzhydryl-3-ethylazetidine.

13.6 g of 3-amino-1-benzhydryl-3-ethylazetidine were obtained in the form of a yellow oil from 24.6 g of 1-benzhydryl-3-ethyl-3-(methanesulphonyloxy)azetidine dissolved in 174 cm³ of 15% solution of ammonia in ethanol. The product isolated was used without further purification for the subsequent steps.

24.6 g of 1-benzhydryl-3-ethyl-3-(methanesulphonyloxy)-azetidine were obtained in the form of a yellow solid, melting point 68° C., from 35.5 g of 1-benzhydryl-3-hydroxy-3-ethyl-azetidine.

35.5 g of 1-benzhydryl-3-hydroxy-3-ethylazetidine were obtained in the form of a yellow oil from 44 g of 1-benzhydryl-3-oxoazetidine and 80 cm³ of ethylmagnesium bromide at a concentration of 399 g per liter in ether.

Example 33

8-(3-Amino-3-ethyl-1-azetidinyl)-1-cyclopropyl-7-fluoro-4-oxo-1,4-dihydrobenzo[b][1,8 ]-naphthyridine-3-carboxylic acid methanesulphonate was prepared under the conditions of Example 15, but starting with 1.8 g of 7,8-difluoro-1-cyclopropyl-4-oxo-1,4-dihydrobenzo[b][1,8]naphthyridine-3-carboxylic acid and 2.94 g of 3-amino-3-ethylazetidine dimethanesulphonate. After recrystallization in dimethylformamide, the product obtained, suspended in 20 cm³ of ethanol, is treated with 3.4 cm³ of a solution at a concentration of 9.6 g % of methanesulphonic acid in ethanol. The suspension is stirred for 5 minutes at approximately 80° C., cooled to a temperature in the region of 20° C., drained and washed with 3 times 10 cm³ of ethanol. 0.55 g of 8-(3-amino-3-ethyl-1-azetidinyl)-1-cyclopropyl-7-fluoro-4-oxo-1,4-dihydrobenzo[b][1,8]naphthyridine-3-carboxylic acid methanesulphonate is obtained in the form of a yellow solid, which decomposes at 248° C.

Example 34

7-Fluoro-1-methyl-8-[3-(1-pyrrolidinyl)-1-azetidinyl]-4-oxo-1,4-dihydrobenzo[b][1,8 ]-naphthyridine-3-carboxylic acid was prepared under the conditions of Example 2, but starting with 1.2 g of 3-ethoxy-carbonyl-7-fluoro-1-methyl-8-[3-(1 -pyrrolidinyl)-1-azetidinyl]-4-oxo-1,4 -dihydrobenzo[b][1,8]naphthyridine. 0.7 g of 7-fluoro-1-methyl-8-3-(1-pyrrolidinyl)-1-azetidinyl]-4-oxo-1,4 -dihydrobenzo[b][1,8]naphthyridine-3-carboxylic acid is obtained in the form of a yellow solid, which decomposes at 302° C.

3-Ethoxycarbonyl-7-fluoro-1-methyl-8-[3-(1 -pyrrolidinyl)-1-azetidinyl]-4-oxo-1,4 -dihydrobenzo[b][1,8]naphthyridine was prepared under the conditions of Example 2, but starting with 1.6 g of 3-ethoxycarbonyl-7,8-difluoro-1-methyl-4-oxo-1,4-dihydrobenzo[b][1,8]naphthyridine and 1.5 g of 3-(1-pyrrolidinyl)azetidine dihydrochloride. The reaction mixture is stirred for 24 hours at approximately 95° C. 1.3 g of 3-ethoxy-carbonyl-7-fluoro-1-methyl-8-[3-(1-pyrrolidinyl)-1-azetidinyl]-4-oxo-1,4-dihydrobenzo[b][1,8] naphthyridine are obtained in the form of a yellow solid, melting point 246° C.

3-(1-Pyrrolidinyl)azetidine was prepared in the form of the dihydrochloride, melting point 195° C., under the conditions described in Japanese Patent Application 74 109 369.

Example 35

8-(3-Cyclopropylamino-1-azetidinyl)-7-fluoro-1-methyl-4-oxo-1,4-dihydrobenzo[b][1,8]naphthyridine was prepared under the conditions of Example 2, but starting with 1.3 g of 8-(3-cyclopropylamino-1-azetidinyl)-3-ethoxycarbonyl-7-fluoro-1-methyl-4-oxo-1,4-dihydro-benzo[b][1,8]naphthyridine. 0.8 g of 8-(3-cyclopropyl-amino-1-azetidinyl)-7-fluoro-1-methyl-4–1,4-dihydrobenzo[b][1,8]naphthyridine is obtained in the form of a yellow solid, which decomposes at 272° C.

8-(3-Cyclopropylamino-1-azetidinyl)-3 -ethoxycarbonyl-7-fluoro-1-methyl-4-oxo-1,4-dihydrobenzo[b][1,8]naphthyridine was prepared under the conditions of Example 15, but starting with 1.45 g of 3-ethoxycarbonyl-7,8-difluoro-1-methyl-4-oxo-1,4-dihydrobenzo[b][1,8]naphthyridine and 1.7 g of 3-(cyclopropylamino)azetidine dihydrochloride. 1.35 g of 8-(3-cyclopropylamino-1-azetidinyl)3-ethoxycarbonyl-7-fluoro-1-methyl-4-oxo-1,4-dihydrobenzo[b][1,8] naphthyridine are obtained in the form of a yellow solid, melting point 221° C. and then 245° C.

3-(Cyclopropylamino)azetidine dihydrochloride was prepared under the conditions described in Example 9 for 3-(ethylamino)azetidine dihydrochloride, but starting with 5.4 g of 1-benzhydryl-3-(cyclopropylamino)azetidine dihydrochloride. 2.25 g of 3-(cyclopropylamino)azetidine dihydrochloride are obtained in the form of a colorless solid, melting point 140° C.

1-Benzhydryl-3-(cyclopropyamino)azetidine dihydrochloride was prepared under the conditions described in Example 9 for 1-benzhydryl-3-(ethylamino)azetiine dihydrochloride, but starting with 15 g of 1-benzhydryl-3-(methanesulphonyloxy)azetidine and 8.2 g of cyclopropylamine. 5.4 g of 1-benzhydryl-3-(cyclopropyl-amino)azetidine dihydrochloride are obtained in the form of a colorless solid, melting point 182° C.

Example 36

Using the procedure described in the above examples, the following products are prepared:

7-Fluoro-1-methyl-8-(3-methylamino-1-azetidinyl)-4-oxo-1,4-dihydrobenzo[b][1,8]naphthyridine-3-carboxylic acid;

8-[3-(2-Aminoethyl)amino-1-azetidinyl]-7-fluoro-1 -methyl-4-oxo-1,4-dihydrobenzo[b][1,8]naphthyridine-3-carboxylic acid;

7-Fluoro-8-[3-(2-hydroxyethyl)amino-1-azetidinyl]-1-methyl-4-oxo-1,4-dihydrobenzo[b][1,8]naphthyridine-3 -carboxylic acid;

7-Fluoro-1-methyl-4-oxo-8-[3-(1-piperazinyl)-1-azetidinyl]-1,4-dihydrobenzo[b][1,8]naphthyridine-3-carboxylic acid;

8-{3-[4-(2-Aminoethyl)phenyl]amino-1-azetidinyl}-7-fluoro-1-methyl-4-oxo-1,4-dihydrobenzo[b]-[1,8]naphthyridine-3-carboxylic acid;

8-(3-Amino-3-phenyl-1-azetidinyl)-7-fluoro-1-methyl-4-oxo-1,4-dihydrobenzo[b][1,8]naphthyridine-3-carboxylic acid;

8-(3-Amino-2-dimethylamino-1-azetidinyl)-7-fluoro-1-methyl-4-oxo-1,4-dihydrobenzo[b][1,8]naphthyridine-3-carboxylic acid;

1-Ethyl-7-fluoro-8-(3-methylamino-1-azetidinyl)-4-oxo-1,4-dihydrobenzo[b][1,8]naphthyridine-3-carboxylic acid;

8-(3-Ethylamino-1-azetidinyl)-1-ethyl-7-fluoro-4-oxo-1,4-dihydrobenzo[b][1,8]naphthyridine-3-carboxylic acid;

8-[3-(2-Aminoethyl)amino-1-azetidinyl]-1-ethyl-7-fluoro-4-oxo-1,4-dihydrobenzo[b][1,8]naphthyridine-3-carboxylic acid;

1-Ethyl-7-fluoro-8-[3-(2-hydroxyethyl)amino-1-azetidinyl]-4-oxo-1,4-dihydrobenzo[b][1,8]-naphthyridine-3-carboxylic acid;

8-(3-Cyclopropylamino-2-azetidinyl)-1-ethyl-7-fluoro-4-oxo-1,4-dihydrobenzo[b][1,8]naphthyridine-3-carboxylic acid;

1-Ethyl-7-fluoro-4-oxo-8-[3-(1-piperazinyl)-1-azetidinyl]-1,4-dihydrobenzo[b][1,8]naphthyridine-3-carboxylic acid;

8-{3-[4-(2-Aminoethyl)phenyl]amino-1-azetidinyl}-1-ethyl-7-fluoro-4-oxo-1,4-dihydrobenzo[b][1,8]-naphthyridine-3-carboxylic acid;

8-(3-Amino-3-phenyl-1-azetidinyl)-1-ethyl-7-fluoro-4-oxo-1,4-dihydrobenzo[b][1,8]naphthyridine-3-carboxylic acid;

8-(3-Amino-2-dimethylamino-1-azetidinyl)-1-ethyl-7-fluoro-4-oxo-1,4-dihydrobenzo[b][1,8]naphthyridine-3-carboxylic acid;

1-Cyclopropyl-8-(3-ethylamino-1-azetidinyl)-7-fluoro-4-oxo-1,4-dihydrobenzo[b][1,8]naphthyridine-3-carboxylic acid;

8-[3-(2-Aminoethyl)amino-1-azetidinyl]-1-cyclopropyl-7-fluoro-4-oxo-1,4-dihydrobenzo[b][1,8]-naphthyridine-3-carboxylic acid;

1-Cyclopropyl-7-fluoro-8-[3-(2-hydroxyethyl)-amino-1-azetidinyl]-4-oxo-1,4-dihydrobenzo[b][1,8]-naphthyridine-3-carboxylic acid;

1-Cyclopropyl-8-(3-cyclopropylamino-1-azetidinyl)-7-fluoro-4-oxo-1,4-dihydrobenzo[b][1,8]naphthyridine-3-carboxylic acid;

1-Cyclopropyl-7-fluoro-4-oxo-8-[3-(1-piperazinyl)-1-azetidinyl]1,4-dihydrobenzo[b][1,8]naphthyridine-3-carboxylic acid;

8-{3-[4-(2-Aminoethyl)phenyl]amino-1-azetidinyl}-1-cyclopropyl-7-fluoro-4-oxo-1,4-dihydrobenzo[b][1,8]naphthyridine-3-carboxylic acid;

8-(3-Amino-3-phenyl-1-azetidinyl)-1-cyclopropyl-7-fluoro-4-oxo-1,4-dihydrobenzo[b][1,8]naphthyridine-3-carboxylic acid;

8-(3-Amino-2-dimethylamino-1-azetidinyl)-1-cyclopropyl-7-fluoro-4-oxo-1,4-dihydrobenzo[b][1,8]-naphthyridine-3-carboxylic acid;

7-Fluoro-1-methylamino-8-(3-methylamino-1-azetidinyl)-4-oxo-1,4-dihydrobenzo[b][1,8]-naphthyridine-3-carboxylic acid;

8-(3-Ethylamino-1-azetidinyl)-7-fluoro-1-methyl-amino-4-oxo-1,4-dihydrobenzo[b][1,8]naphthyridine-3-carboxylic acid;

8-[3-(2-Aminoethyl)amino-1-azetidinyl]-7-fluoro-1-methylamino-4-oxo-1,4-dihydrobenzo[b][1,8]-naphthyridine-3-carboxylic acid;

7-Fluoro-8-[3-(2-hydroxyethyl)amino-1-azetidinyl]-1-methylamino-4-oxo-1,4-dihydrobenzo[b][1,8]-naphthyridine-3-carboxylic acid;

8-(3-Cyclopropylamino-1-azetidinyl)-7-fluoro-1-methylamino-4-oxo-1,4-dihydrobenzo[b][1,8]-naphthyridine-3-carboxylic acid;

7-Fluoro-1-methylamino-4-oxo-8-[3-(1-piperazinyl)-1-azetidinyl]1,4-dihydrobenzo[b][1,8]naphthyridine-3-carboxylic acid;

8-{3-[4-(2-Aminoethyl)phenyl]amino-1-azetidinyl}-7-fluoro-1-methylamino-4-oxo-1,4-dihydrobenzo[b][1,8]-naphthyridine-3-carboxylic acid;

8-(3-Amino-3-phenyl-1-azetidinyl)-7-fluoro-1-methylamino-4-oxo-1,4-dihydrobenzo[b][1,8]-naphthyridine-3-carboxylic acid;

8-(3-Amino-3-methyl-1-azetidinyl)-7-fluoro-1-methylamino-4-oxo-1,4-dihydrobenzo[b][1,8]naphthyridine-3-carboxylic acid;

8-(3-Amino-2-dimethylamino-1-azetidinyl)-7-fluoro-1-methylamino-4-oxo-1,4-dihydrobenzo[b][1,8]-naphthyridine-3-carboxylic acid;

7-Fluoro-1-(2-fluoroethyl)-8-(3-methylamino-1-azetidinyl)-4-oxo-1,4-dihydrobenzo[b][1,8]-naphthyridine-3-carboxylic acid;

8-(3-Ethylamino-1-azetidinyl)-7-fluoro-1-(2-fluoroethyl)-4-oxo-1,4-dihydrobenzo[b][1,8]-naphthyridine-3-carboxylic acid;

8-[3-(2-Aminoethyl)amino-1-azetidinyl]-7-fluoro-1-(2-fluoroethyl)-4-oxo-1,4-dihydrobenzo[b][1,8]-naphthyridine-3-carboxylic acid;

7-Fluoro-1-(2-fluoroethyl)-8-[3-(2-hydroxyethyl)-amino-1-azetidinyl]-4-oxo-1,4-dihydrobenzo[b][1,8]-naphthyridine-3-carboxylic acid;

8-(3-Cyclopropylamino-1-azetidinyl)-7-fluoro-1-(2-fluoroethyl)-4-oxo-1,4-dihydrobenzo[b][1,8]-naphthyridine-3-carboxylic acid;

7-Fluoro-1-(2-fluoroethyl)-4-oxo-8-[3-(1-piperazinyl)-1-azetidinyl]1,4-dihydrobenzo[b][1,8]-naphthyridine-3-carboxylic acid;

8-{3-[4-(2-Aminoethyl)phenyl]amino-1-azetidinyl}-7-fluoro-1-(2-fluoroethyl)-4-oxo-1,4-dihydrobenzo[b][1,8]naphthyridine-3-carboxylic acid;

8-(3-Amino-3-phenyl-1-azetidinyl)-7-fluoro-1-(2-fluoroethyl)-4-oxo-1,4-dihydrobenzo[b][1,8]-naphthyridine-3-carboxylic acid;

8-(3-Amino-3-methyl-1-azetidinyl)-7-fluoro-1-(2-fluoroethyl)-4-oxo-1,4-dihydrobenzo[b][1,8]-naphthyridine-3-carboxylic acid;

8-(3-Amino-2-dimethylamino-1-azetidinyl)-7-fluoro-1-(2-fluoroethyl)-4-oxo-1,4-dihydrobenzo[b][1,8]-naphthyridine-3-carboxylic acid;

7-Fluoro-8-(3-methylamino-1-azetidinyl)-4-oxo-1-t-butyl-1,4-dihydrobenzo[b][1,8]naphthyridine-3-carboxylic acid;

8-(3-Ethylamino-1-azetidinyl)-7-fluoro-4-oxo-1-t-butyl-1,4-dihydrobenzo[b][1,8]naphthyridine-3-carboxylic acid;

8-[3-(2-Aminoethyl)amino-1-azetidinyl]-7-fluoro-4-oxo-1-t-butyl-1,4-dihydrobenzo[b][1,8]naphthyridine-3-carboxylic acid;

7-Fluoro-8-[3-(2-hydroxyethyl)amino-1-azetidinyl]-4-oxo-1-t-butyl-1,4-dihydrobenzo[b][1,8]naphthyridine-3-carboxylic acid;

8-(3-Cyclopropylamino-1-azetidinyl)-7-fluoro-4-oxo-1-t-butyl-1,4-dihydrobenzo[b][1,8]naphthyridine-3-carboxylic acid;

7-Fluoro-4-oxo-8-[3-(1-piperazinyl)-1-azetidinyl]-1-t-butyl-1,4-dihydrobenzo[b][1,8]naphthyridine-3-carboxylic acid;

8-{3-[4-(2-Aminoethyl)phenyl]amino-1-azetidinyl}-7-fluoro-4-oxo-1-t-butyl-1,4-dihydrobenzo[b][1,8]naphthyridine-3-carboxylic acid;

8-(3-Amino-3-phenyl-1-azetidinyl)-7-fluoro-4-oxo-1-t-butyl-1,4-dihydrobenzo[b][1,8]naphthyridine-3-carboxylic acid;

8-(3-Amino-3-methyl-1-azetidinyl)-7-fluoro-4-oxo-1-t-butyl-1,4-dihydrobenzo[b][1,8]naphthyridine-3-carboxylic acid;

8-(3-Amino-2-dimethylamino-1-azetidinyl)-7-fluoro-4-oxo-1-t-butyl-1,4-dihydrobenzo[b][1,8]naphthyridine-3-carboxylic acid;

7,9-Difluoro-8-(3-ethylamino-1-azetidinyl)-1-methyl-4-oxo-1,4-dihydrobenzo[b][1,8]naphthyridine-3-carboxylic acid;

8-[3-(2-Aminoethyl)amino-1-azetidinyl]-7,9-difluoro-1-methyl-4-oxo-1,4-dihydrobenzo[b][1,8]-naphthyridine-3-carboxylic acid;

7,9-Difluoro-[3-(2-hydroxyethyl)amino-1-azetidinyl]-1-methyl-4-oxo-1,4-dihydrobenzo[b][1,8]-naphthyridine-3-carboxylic acid;

8-(3-Cyclopropylamino-1-azetidinyl)-7,9-difluoro-1-methyl-4-oxo-1,4-dihydrobenzo[b][1,8]naphthyridine-3-carboxylic acid;

7,9-Difluoro-1-methyl-4-oxo-8-[3-(1-piperazinyl)-1-azetidinyl]1,4-dihydrobenzo[b][1,8]naphthyridine-3-carboxylic acid;

8-{3-[4-(2-Aminoethyl)phenyl]amino-1-azetidinyl}-7,9-difluoro-1-methyl-4-oxo-1,4-dihydrobenzo[b][1,8]-naphthyridine-3-carboxylic acid;

8-(3-Amino-3-phenyl-1-azetidinyl)-7,9-difluoro-1-methyl-4-oxo-1,4-dihydrobenzo[b][1,8]naphthyridine-3-carboxylic acid;

8-(3-Amino-2-dimethylamino-1-azetidinyl)-7,9-difluoro-1-methyl-4-oxo-1,4-dihydrobenzo[b][1,8]-naphthyridine-3-carboxylic acid;

7,9-Difluoro-1-ethyl-8-(3-methylamino-1-azetidinyl)-4-oxo-1,4-dihydrobenzo[b][1,8]-naphthyridine-3-carboxylic acid;

8-(3-Ethylamino-1-azetidinyl)-7,9-difluoro-1-ethyl-4-oxo-1,4-dihydrobenzo[b][1,8]naphthyridine-3-carboxylic acid;

8-[3-(2-Aminoethyl)-1-azetidinyl]-7,9-difluoro-1-ethyl-4-oxo-1,4-dihydrobenzo[b][1,8]naphthyridine-3-carboxylic acid;

7,9-Difluoro-1-ethyl-8-[3-(2-hydroxyethyl)-1-azetidinyl]-4-oxo-1,4-dihydrobenzo[b][1,8]-naphthyridine-3-carboxylic acid;

8-(3-Cyclopropylamino-1-azetidinyl)-7,9-difluoro-1-ethyl-4-oxo-1,4-dihydrobenzo[b][1,8]naphthyridine-3-carboxylic acid;

7,9-Difluoro-1-ethyl-4-oxo-8-[3-(1-piperazinyl)-1-azetidinyl]-1,4-dihydrobenzo[b][1,8]naphthyridine-3-carboxylic acid;

8-}3-[4-(2-Aminoethyl)phenyl]amino-1-azetidinyl}-7,9-difluoro-1-ethyl-4-oxo-1,4-dihydrobenzo[b][1,8]-naphthyridine-3-carboxylic acid;

8-(3-Amino-3-phenyl-1-azetidinyl)-7,9-difluoro-1-ethyl-4-oxo-1,4-dihydrobenzo[b][1,8]naphthyridine-3-carboxylic acid;

8-(3-Amino-3-methyl-1-azetidinyl)-7,9-difluoro-1-ethyl-4-oxo-1,4-dihydrobenzo[b][1,8]naphthyridine-3-carboxylic acid;

8-(3-Amino-2-dimethylamino-1-azetidinyl)-7,9 difluoro-1-ethyl-4-oxo-1,4-dihydrobenzo[b][1,8]-naphthyridine-3-carboxylic acid;

1-Cyclopropyl-7,9-difluoro-8-(3-methylamino-1-azetidinyl)-4-oxo-1,4-dihydrobenzo[b][1,8]-naphthyridine-3-carboxylic acid;

1-Cyclopropyl-8-(3-ethylamino-1-azetidinyl)-7,9-difluoro-4-oxo-1,4-dihydrobenzo[b][1,8]naphthyridine-3-carboxylic acid;

8-[3-(2-Aminoethyl)amino-1-azetidinyl]-1-cyclopropyl-7,8-difluoro-4-oxo-1,4-dihydrobenzo[b][1,8]-naphthyridine-3-carboxylic acid;

1-Cyclopropyl-7,9-difluoro-8-[3-(2-hydroxyethyl)-amino-1-azetidinyl]-4-oxo-1,4-dihydrobenzo[b][1,8]-naphthyridine-3-carboxylic acid;

1-Cyclopropyl-8-(3-cyclopropylamino-1-azetidinyl)-7,8-difluoro-4-oxo-1,4-dihydrobenzo[b][1,8]-naphthyridine-3-carboxylic acid;

1-Cyclopropyl-7,9-difluoro-4-oxo-8-[3-(1-piperazinyl)-1-azetidinyl]1,4-dihydrobenzo[b][1,8]-naphthyridine-3-carboxylic acid;

8-{3-[4-(2-Aminoethyl)phenyl]amino-1-azetidinyl}-1-cyclopropyl-7,9-difluoro-4-oxo-1,4-dihydrobenzo[b][1,8]naphthyridine-3-carboxylic acid;

8-(3-Amino-3-phenyl-1-azetidinyl)-1-cyclopropyl-7,9-difluoro-4-oxo-1,4-dihydrobenzo[b][1,8]-naphthyridine-3-carboxylic acid;

8-(3-Amino-3-methyl-1-azetidinyl)-1-cyclopropyl-7,9-difluoro-4-oxo-1,4-dihydrobenzo[b][1,8]-naphthyridine-3-carboxylic acid;

8-(3-Amino-2-dimethylamino-1-azetidinyl)-1-cyclopropyl-7,8-difluoro-4-oxo-1,4-dihydrobenzo[b][1,8]-naphthyridine-3-carboxylic acid;

7,9-Difluoro-1-methylamino-8-(3-methylamino-1-azetidinyl)-4-oxo-1,4-dihydrobenzo[b][1,8]-naphthyridine-3-carboxylic acid;

8-(3-Ethylamino-1-azetidinyl)-7,9-difluoro-1-methylamino-4-oxo-1,4-dihydrobenzo[b][1,8]-naphthyridine-3-carboxylic acid;

8-[3-(2-Aminoethyl)amino-1-azetidinyl]-7,9-difluoro-1-methylamino-4-oxo-1,4-dihydrobenzo[b][1,8]naphthyridine-3-carboxylic acid;

7,9-Difluoro-8-[3-(2-hydroxyethyl)amino-1-azetidinyl-]-1-methylamino-4-oxo-1,4-dihydrobenzo[b][1,8]naphthyridine-3-carboxylic acid;

8-(3-Cyclopropylamino-1-azetidinyl)-7,9-difluoro-1-methylamino-4-oxo-1,4-dihydrobenzo[b][1,8]-naphthyridine-3-carboxylic acid;

7,9-Difluoro-1-methylamino-4-oxo-8-[3-(1-piperazinyl)-1-azetidinyl]1,4-dihydrobenzo[b][1,8]-naphthyridine-3-carboxylic acid;

8-}3-[4-(2-Aminoethyl)phenyl]amino-1-azetidinyl}-7,9-difluoro-1-methylamino-4-oxo-1,4-dihydrobenzo[b][1,8]naphthyridine-3-carboxylic acid;

8-(3-Amino-3-phenyl-1-azetidinyl)-7,9-difluoro-1-methylamino-4-oxo-1,4-dihydrobenzo[b][1,8]-naphthyridine-3-carboxylic acid;

8-(3-Amino-3-methyl-1-azetidinyl)-7,9-difluoro-1-methylamino-4-oxo-1,4-dihydrobenzo[b][1,8]-naphthyridine-3-carboxylic acid;

8-(3-Amino-2-dimethylamino-1-azetidinyl)-7,9-difluoro-1-methylamino-4-oxo-1,4-dihydrobenzo[b][1,8]-naphthyridine-3-carboxylic acid;

7,9-Difluoro-1-(2-fluoroethyl)-8-(3-methylamino-1-azetidinyl)-4-oxo-1,4-dihydrobenzo[b][1,8]-naphthyridine-3-carboxylic acid;

7,9-Difluoro-8-(3-ethylamino)-1-azetidinyl)-1-(2-fluoroethyl)-4-oxo-1,4-dihydrobenzo[b][1,8]-naphthyridine-3-carboxylic acid;

8-[3-(2-Aminoethyl)amino-1-azetidinyl]-7,9-difluoro-1-(2-fluoroethyl)-4-oxo-1,4-dihydrobenzo[b][1,8]naphthyridine-3-carboxylic acid;

7,9-Difluoro-1-(2-fluoroethyl)-8-[3-(2-hydroxyethyl)amino-1-azetidinyl]-4-oxo-1,4-dihydrobenzo-[b][1,8]naphthyridine-3-carboxylic acid;

8-(3-Cyclopropylamino-1-azetidinyl)-7,9-difluoro-1-(2-fluoroethyl)-4-oxo-1,4-dihydrobenzo[b][1,8]-naphthyridine-3-carboxylic acid;

7,9-Difluoro-1-(2-fluoroethyl)-4-oxo-8-[3-(1-piperazinyl)-1-azetidinyl]1,4-dihydrobenzo[b][1,8]-naphthyridine-3-carboxylic acid;

8-{3-[4-(2-Aminoethyl)phenyl]amino-1-azetidinyl}-7,9-difluoro-1-(2-fluoroethyl)-4-oxo-1,4-dihydrobenzo[b][1,8]naphthyridine-3-carboxylic acid;

8-(3-Amino-3-phenyl-1-azetidinyl)-7,9-difluoro-1-(2-fluoroethyl)-4-oxo-1,4-dihydrobenzo[b][1,8]-naphthyridine-3-carboxylic acid;

8-(3-Amino-3-methyl-1-azetidinyl)-7,9-dfluoro-1-(2-fluoroethyl)-4-oxo-1,4-dihydrobenzo[b][1,8]-naphthyridine-3-carboxylic acid;

8-(3-Amino-2-dimethylamino-1-azetidinyl)-7,9-difluoro-1-(2-fluoroethyl)-4-oxo-1,4-dihydrobenzo[b][1,8]naphthyridine-3-carboxylic acid;

7-Fluoro-8-(3-methylamino-1-azetidinyl)-4-oxo-1-t-butyl-1,4-dihydrobenzo[b][1,8]naphthyridine-3-carboxylic acid;

8-(3-Ethylamino-1-azetidinyl)-7-fluoro-4-oxo-1-t-butyl-1,4-dihydrobenzo[b][1,8]naphthyridine-3-carboxylic acid;

8-[3-(2-Aminoethyl)amino-1-azetidinyl]-7,9-difluoro-4-oxo-1-t-butyl-1,4-dihydrobenzo[b][1,8]-naphthyridine-3-carboxylic acid;

7,9-Difluoro-8-[3-(2-hydroxyethyl)amino-1-azetidinyl]-4-oxo-1-t-butyl-1,4-dihydrobenzo[b][1,8]-naphthyridine-3-carboxylic acid;

8-(3-Cyclopropylamino-1-azetidinyl)-7,9-difluoro-4-oxo-1-t-butyl-1,4-dihydrobenzo[b][1,8]naphthyridine-3-carboxylic acid;

7,9-Difluoro-4-oxo-8-[3-(1-piperazinyl)-1-azetidinyl]-1-t-butyl-1,4-dihydrobenzo[b][1,8]-naphthyridine-3-carboxylic acid;

8-{3-[4-(2-Aminoethyl)phenyl]amino-1-azetidinyl}-7,8-difluoro-4-oxo-1-t-butyl-1,4-dihydrobenzo[b][1,8]-naphthyridine-3-carboxylic acid;

8-(3-Amino-3-phenyl-1-azetidinyl)-7,9-difluoro-4-oxo-1-t-butyl-1,4-dihydrobenzo[b][1,8]naphthyridine-3-carboxylic acid;

8-(3-Amino-3-methyl-1-azetidinyl)-7,9-difluoro-4-oxo-1-t-butyl-1,4-dihydrobenzo[b][1,8]naphthyridine-3-carboxylic acid;

8-(3-Amino-2-dimethylamino-1-azetidinyl)-7,9-difluoro-4-oxo-1-t-butyl-1,4-dihydrobenzo[b][1,8]-naphthyridine-3-carboxylic acid.

The present invention also relates to pharmaceutical compositions which can be used in human or veterinary medicine, containing as active product at least one product of general formula (I) in the pure state (in free form or in salt form) or in the form of a combination with one or more compatible and pharmaceutically acceptable diluents or adjuvants. These compositions may be used orally, parenterally or rectally.

As solid compositions for oral administration, tablets, hard gelatin capsules, pills, powders or granules may be used. In these compositions, the active product according to the invention may be mixed with one or more inert diluents or adjuvants such as sucrose, lactose or starch. These compositions can also comprise substances other than diluents, e.g. a lubricant such as magnesium stearate.

As liquid compositions for oral administration, it is possible to use solutions, suspensions, syrups, elixirs and pharmaceutically acceptable emulsions, containing inert diluents such as water or liquid paraffin. These compositions can also comprise substances other than diluents, e.g. wetting, sweetening or flavoring products.

The compositions for parenteral administration can be suspensions, emulsions or sterile, aqueous or non-aqueous solutions. As a solvent or vehicle, propylene glycol, a polyethylene glycol, vegetable oils, especially olive oil, and injectable organic esters, e.g. ethyl oleate, may be employed. These compositions can also contain adjuvants, especially wetting, emulsifying, dispersing or tonicity agents. The sterilization may be carried out in several ways, e.g. using a bacteriological filter, by incorporating sterilizing agents in the composition, by irradiation or by heating. They may also be prepared in the form of sterile solid compositions which will be dissolved at the time of use in sterile water or any other sterile injectable medium.

The compositions for rectal administration are suppositories or rectal capsules which can contain, apart from the active product, excipients such as cocoa butter or Suppocire.

In human or veterinary therapy, the compositions according to the invention are especially useful in the treatment of infections of bacterial origin.

Generally speaking, the doctor will determine the dosage he considers most suitable in accordance with the age, weight, degree of infection and other factors specific for the subject to be treated. Generally, the doses are between 0.2 and 1 g of active product twice a day, administered orally or parenterally, for an adult.

The example which follows, given without implied limitation, illustrates a composition according to the invention:

EXAMPLE

Tablets containing 250 mg of active product and having the following composition are prepared according to the customary techniques:

8-(3-Amino-1-azetidinyl)-1-cyclopropyl-7 -fluoro-1-methyl-4-oxo-1,4 -dihydrobenzo-[b][1,8]naphthyridine-3-carboxylic acid 250 mg Starch 50 mg Lactose 35 mg Talc 15 mg The products of general formula (I) are also advantageous in the agrochemical field, for antibacterial treatment of plants and crops. It is understood that the compositions for agrochemical use contain a product of general formula (I) also falling within the scope of the present invention.

Moreover, the products of general formula (I) may also be used as agents for the preservation or disinfection of organic or inorganic substances; in particular, in the dyestuffs, fat, paper, wood or polymer industry or alternatively in the textiles industry, the food industry or water treatment. It is also understood that the compositions containing a product of general formula (I), in the pure state or in the form of a combination with compatible diluents or adjuvants, also fall within the scope of the present invention.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. A benzo[b][1,8]naphthyridine compound having the formula:

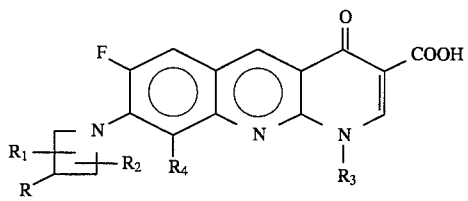

in which

R represents a hydrogen atom or an amino radical or an alkylamino radical in which the alkyl portion is optionally substituted with an amino or hydroxyl radical, or represents a dialkylamino radical in which the alkyl portions, with the nitrogen atom to which they are attached, optionally form a 5- or 6-membered heterocycle optionally containing another hetero atom selected from nitrogen, oxygen and sulphur, or represents a (3- to 6-membered cycloalkyl)-amino radical, or an alkanoylamino, N-alkyl-N-alkanoyl-amino or aminoalkylphenylamino radical, $R_1$ and $R_2$, which may be identical or different, are located, respectively, at positions 2 and 3 and represent hydrogen atoms, alkyl radicals, alkenyl radicals containing 2 to 4 carbon atoms, phenyl radicals or phenyl radicals substituted with a halogen atom or with an alkyl, alkyloxy, hydroxyl, nitro, amino, alkylamino, dialkylamino or haloalkyl radical, or alternatively $R_1$ and $R_2$ are located at position 2 and represent alkyl radicals, provided R, $R_1$ and $R_2$ are not simultaneously a hydrogen atom, $R_3$ represents a hydrogen atom or an alkyl, or carboxyalkyl radical, a cycloalkyl radical containing 3 to 6 carbon atoms, and $R_4$ represents a hydrogen atom or a fluorine atom, the alkyl, alkanoylamino, and N-alkyl-N-alkanoyl-amino radicals mentioned above being unbranched or branched and containing 1 to 4 carbon atoms, in its stereoisomeric forms, a metal salt thereof, an addition salt thereof with a nitrogenous base, an addition salt thereof with an acid or a hydrated form thereof.

2. A benzo[b][1,8]naphthyridine compound having the formula:

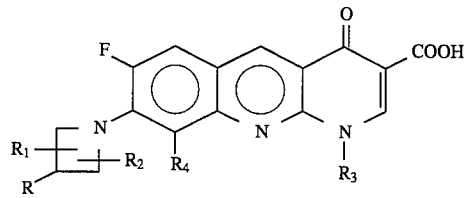

in which

R represents a hydrogen atom or an amino radical or an alkylamino radical in which the alkyl portion is optionally substituted with an amino or hydroxyl radical, or represents a dialkylamino radical in which the alkyl portions, with the nitrogen atom to which they are attached, form a 5- or 6-membered heterocycle optionally containing another hetero atom selected from nitrogen, oxygen and sulphur, or represents a (3- to 6-membered cycloalkyl)-amino radical, or an alkanoylamino, N-alkyl -N-alkanoyl-amino or aminoalkylphenylamino radical, $R_1$ and $R_2$, which may be identical or different, are located, respectively, at positions 2 and 3 and represent hydrogen atoms, alkyl radicals, alkenyl radicals containing 2 to 4 carbon atoms, phenyl radicals or phenyl radicals substituted with a halogen atom or with an alkyl, alkyloxy, hydroxyl, nitro, amino, alkylamino, dialkylamino or haloalkyl radical, or alternatively $R_1$ and $R_2$ are located at position 2 and represent alkyl radicals, provided R, $R_1$ and $R_2$ are not simultaneously a hydrogen atom, $R_3$ represents a hydrogen atom or an alkyl, or carboxyalkyl radical, a cycloalkyl radical containing 3 to 6 carbon atoms, and $R_4$ represents a hydrogen atom or a fluorine atom, the alkyl, alkanoylamino, and N-alkyl-N-alkanoyl-amino radicals mentioned above being unbranched or branched and containing 1 to 4 carbon atoms.

3. A composition comprising a compound, a salt thereof, or a hydrated form thereof according to claim 1 in the pure state, or in combination with a compatible diluent or adjuvant.

4. A compound of 8-(3-amino-1-azetidinyl)-1-cyclopropyl-7-fluoro-4-oxo-1,4-dihydrobenzo[b][1,8]-naphthyridine-3-carboxylic acid.

5. A compound according to claim 2, wherein the derivative is 8-(trans-3-amino-2-methyl-1-azetidinyl])-1 -cyclopropyl-7-fluoro-4-oxo-1,4-dihydrobenzo[b][1,8]naphthyridine-3-carboxylic acid.

6. A compound according to claim 2, wherein the derivative is 8-(3-amino-3-propyl-1-azetidinyl)-7-fluoro-1-methyl-4-oxo-1,4-dihydrobenzo[b][1,8]naphthyridine-3-carboxylic acid.

7. A compound according to claim 2, wherein the derivative is 8-(3-amino-3-methyl-1-azetidinyl)-7-fluoro-1 -methyl-4-oxo-1,4-dihydrobenzo[b][1,8]naphthyridine-3-carboxylic acid.

8. A compound according to claim 2, wherein the derivative is 8-(3-amino-3-methyl-1-azetidinyl)-1-ethyl-7-fluoro-4-oxo-1,4-dihydrobenzo[b][1,8]naphthyridine-3-carboxylic acid.

9. A compound according to claim 2, wherein the derivative is 8-(3-amino-3-methyl-1-azetidinyl)-1-cyclopropyl-7-fluoro-4-oxo-1,4-dihydrobenzo[b][1,8]-naphthyridine-3-carboxylic acid.

10. A compound according to claim 2, wherein the derivative is 7-fluoro-1-methyl-8-(3-methyl-3-methylamino-1-azetidinyl)-4-oxo-1,4-dihydrobenzo[b][1,8]-naphthyridine-3-carboxylic acid.

11. A compound according to claim 2, wherein the derivative is 1-cyclopropyl-7-fluoro-8-(3-methyl-3-methylamino-1-azetidinyl)-4-oxo-1,4-dihydrobenzo[b][1,8]naphthyridine-3-carboxylic acid.

12. A compound according to claim 2, wherein the derivative is 8-(3-cyclopropylamino-3-methyl-1-azetidinyl)-7-fluoro-1-methyl-4-oxo-1,4-dihydrobenzo[b][1,8]-naphthydridine-3-carboxylic acid.

13. A compound according to claim 2, wherein the derivative is 8-(3-amino-3-ethyl-1-azetidinyl)-7-fluoro-1-methyl-4-oxo-1,4-dihydrobenzo[b][1,8]naphthyridine-3-carboxylic acid.

14. A compound according to claim 2, wherein the derivative is 8-(3-amino-3-ethyl-1-azetidinyl)-1-cyclopropyl-7-fluoro-4-oxo-1,4-dihydrobenzo[b][1,8]-naphthyiridine-3-carboxylic acid.

* * * * *

UNITED STATES PATENT AND TRADEMARK OFFICE
CERTIFICATE OF CORRECTION

PATENT NO. : 5,556,861
DATED : September 17, 1996
INVENTOR(S) : Eric Bacque, et. al.

It is certified that error appears in the above-indentified patent and that said Letters Patent is hereby corrected as shown below:

Claim 2, column 30, line 48, after "atoms", change "." to --,--, and insert the following:

--in its stereoisomeric forms, a metal salt thereof, an addition salt thereof with a nitrogenous base, an addition salt thereof with an acid or a hydrated form thereof.--

Signed and Sealed this

Fourteenth Day of January, 1997

*Attest:*

BRUCE LEHMAN

*Attesting Officer*     *Commissioner of Patents and Trademarks*